United States Patent
Borowski et al.

(10) Patent No.: US 9,745,335 B2
(45) Date of Patent: Aug. 29, 2017

(54) N-SUBSTITUTED SECOND GENERATION DERIVATIVES OF ANTIFUNGAL ANTIBIOTIC AMPHOTERICIN B AND METHODS OF THEIR PREPARATION AND APPLICATION

(71) Applicant: Blirt S.A., Gdansk (PL)

(72) Inventors: Edward Borowski, Gdasnk (PL); Natalia Salewska, Gdynia (PL); Joanna Boros-Majewska, Gdansk (PL); Maria Milewska, Gdansk (PL); Malgorzata Wysocka, Gdansk (PL); Slawomir Milewski, Gdansk (PL); Izabela Chabowska, Bytow (PL); Michal Sabisz, Gdansk (PL)

(73) Assignee: BLIRT S.A., Gdansk (PL)

( * ) Notice: Subject to any disclaimer, the term of this patent is extended or adjusted under 35 U.S.C. 154(b) by 8 days.

(21) Appl. No.: 14/407,933

(22) PCT Filed: Jun. 14, 2013

(86) PCT No.: PCT/EP2013/062436
§ 371 (c)(1),
(2) Date: Dec. 12, 2014

(87) PCT Pub. No.: WO2013/186384
PCT Pub. Date: Dec. 19, 2013

(65) Prior Publication Data
US 2015/0291648 A1 Oct. 15, 2015

(30) Foreign Application Priority Data
Jun. 15, 2012 (PL) .......................... 399545

(51) Int. Cl.
*C07H 17/08* (2006.01)
(52) U.S. Cl.
CPC .................... *C07H 17/08* (2013.01)
(58) Field of Classification Search
None
See application file for complete search history.

(56) References Cited

U.S. PATENT DOCUMENTS

| | | | |
|---|---|---|---|
| 3,244,590 A | 4/1966 | Schaffner et al. | |
| 3,780,173 A | 12/1973 | Bruzzese et al. | |
| 4,144,328 A | 3/1979 | Vainshtein et al. | |
| 4,195,172 A | 3/1980 | Falkowski et al. | |
| 4,272,525 A * | 6/1981 | Wright ................ | C07H 17/08 514/3.3 |
| 4,396,610 A | 8/1983 | Witzke | |
| 5,314,999 A | 5/1994 | Seman et al. | |
| 5,942,495 A * | 8/1999 | Borowski ............ | C07H 17/08 514/31 |
| 5,981,721 A | 11/1999 | Mohan | |
| 6,413,537 B1 | 7/2002 | Kwon et al. | |
| 6,562,796 B2 | 5/2003 | Baldwin et al. | |
| 6,664,241 B2 | 12/2003 | Chang et al. | |

FOREIGN PATENT DOCUMENTS

| | | |
|---|---|---|
| DE | 2706156 | 8/1978 |
| EP | 0375222 B1 | 6/1990 |
| EP | 0375223 A2 | 6/1990 |
| EP | 2 174 944 | 4/2010 |
| GB | 1387187 | 3/1975 |
| GB | 2027698 | 2/1980 |
| PL | 82224 B | 10/1975 |
| PL | 100966 B | 3/1979 |
| PL | 120035 B | 2/1982 |
| PL | 120111 B | 2/1982 |
| PL | 122884 B | 8/1982 |
| PL | 138831 B | 11/1986 |
| PL | 142847 * | 12/1987 |
| PL | 142847 B | 12/1987 |
| PL | 142848 | 12/1987 |
| PL | 142848 B | 12/1987 |
| PL | 199213 B1 | 8/2001 |
| PL | 210774 B1 | 12/2007 |

(Continued)

OTHER PUBLICATIONS

Belakhov V.V. et al. Khimiko-Farmatsevicheskii Zhurnal. 25(11)45-48, 1991.
Bonner D. P. et al., Polyene macrolide derivatives. III Biological properties of polyene macrolide ester salts, J. Antibiot., 25(4)261-262,1972.
Borgos S. E. F. et al., Probing the structure-function relationship of polyene macrolides: engineered biosynthesis of soluble nystatin analogues, J. Med. Chem., 49(8):2431-2439, 2006.
Borowski E. et al., The complete structure of the polyene macrolide antibiotic nystatin $A_1$, Tetrahedron Lett., 8:685-690, 1971.
Bronin G.O. et al., Pediatryia, 4:31-37, 2004.
Bruzzese T. et al., Partricin methyl ester, a semisynthetic polyene antibiotic, Experientia 28(12):1515-1516, Dec. 15, 1972.

(Continued)

*Primary Examiner* — Traviss C McIntosh, III
(74) *Attorney, Agent, or Firm* — Knobbe Martens Olson & Bear LLP

(57) ABSTRACT

The invention provides semisynthetic N-substituted derivatives of the antifungal antibiotic Amphotericin B and water soluble salts and complexes, pharmaceutical compositions and plant and building treatment products comprising the derivatives and their use as antifungal antibiotics.

Formula 1a

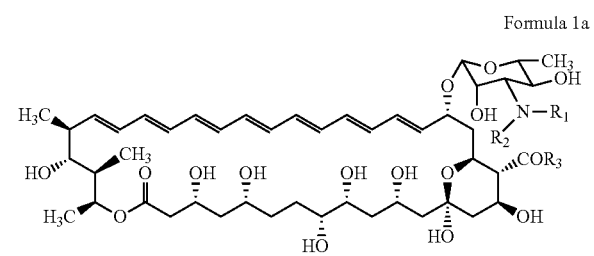

12 Claims, No Drawings

(56) References Cited

FOREIGN PATENT DOCUMENTS

| PL | 199213 B | 8/2008 |
|---|---|---|
| WO | WO 93/17034 A1 | 9/1993 |
| WO | WO 96/35701 A1 | 11/1996 |
| WO | WO 99/51274 | 10/1999 |
| WO | WO 01/51061 A1 | 7/2001 |
| WO | WO 01/68102 | 9/2001 |
| WO | WO 01/91758 A1 | 12/2001 |
| WO | WO 2007/096137 | 8/2007 |
| WO | WO 2007/096137 A1 | 8/2007 |

OTHER PUBLICATIONS

Bruzzese T. et al., Synthesis and biological properties of alkyl esters of polyene antibiotics, J. Pharm. Sci. 64(3):462-463,Mar. 975.

Czerwiński A., N-dimethylaminoacyl derivatives of polyene macrolide antibiotics, The Journal of Antibiotics, 39 (7):1025-1027, Jul. 1986.

Demain A. L. et al., Microbial drug discovery: 80 years of progress, J. Antibiot., 62:5-16, 2009.

Enoch D. A. et al., Invasive fungal infections: a review of epidemiology and management options, J. Med. Microbiol., 55:809-818, 2006.

Falkowski L. et al., Methyl esters of trimethyl-ammonium derivatives of polyene macrolide antibiotics, J. of Antibiotics. 32(10):1080-1081, Oct. 1979.

Falkowski L. et al., The preparation of n-glycosyl derivatives of polyene macrolide antibiotics and their comparative antifungal activities, Acta Polon. Pharm., 37(5):517-520, 1980.

Falkowski L. et al., The preparation of methyl esters of trimethylammonium derivatives of polyenes macrolide antibiotics and their biological properties, Acta Polon. Pharm., 37(6):631-634, 1980.

Falkowski L. et al., N-glocosyl derivatives of polyene macrolide antibiotics, J. Antibiot., 28(3):244-245, Mar. 1975.

Falkowski L. et al., The structure of n-glycosyl derivatives of polyene macrolide antibiotics. The reaction of nystatin with $_D$-glucose, Polish J. Chem., 56:123-130, Jan. 1982.

Franz R. et al., Multiple molecular mechanisms contribute to a stepwise development of fluconazole resistance in clinical candida albicans strains, Antimicrob Agents Chemother., 42(12):3065-3072, Dec. 1998.

Franz et al., Molecular aspects of fluconazole resistance development in Candida albicans, Mycoses, 42:453-458,1999.

Fridkin S. K., Candidemia is costly-plain and simple, Clin. Infect. Dis., 41:1240-1241, Nov. 1, 2005.

Grzybowska et al, Hydrazides—a novel type of derivatives of polyene macrolide antifungal antibiotics, J. Antibiot.,43(7):907-908, Jul. 1990.

Hazen et al., Fungicidin, an antibiotic produced by a soil actinomycete, Proc. Soc. Exptl. Biol., 76:93-97, 1951.

Hazen et al., Two antifungal agents produced by a soil actinomyete, Science, 112, 112, 1950.

Kontoyiannis et al., Antifungal drug resistance of pathogenic fungi, Lancet, 359:1135-1144, Mar. 30, 2002.

Kushnir V.N. et al., Synthesis and antimicrobial activity on n-cinnamoyl and β-substituted N-acryloyl derivatives of urea, Khim. Farm. Zh., 11(1):45-50, Jan. 1977.

Nucii N. et al., Emerging fungal diseases, Clin. Infect Dis., 41:521-526, Aug. 15, 2005.

Paquet et al., Significant improvement of antifungal activity of polyene macrolides by bisalkylation of the mycosamine, Org. Lett., 8(9):1807-1809, 2006.

Patterson, Advances and challenges in management of invasive mycoses, Lancet, 366:1013-1025, Sep. 17, 2005.

Pawlak et al., The structure of Nystatin $A_2$, Polish J. Chem., 79:1673-1679, 2005.

Petersen, Intramolecular fluorescence energy transfer in nitrobenzoxadiazole derivatives of polyene antibiotics, Can. J. Chem. 63 (1):77-85, 1985.

Pfaller M. A. et al., Epidemiology of invasive candidiasis: a persistent public health problem, Clin. Microbiol. Rev. 20(1):133-163, Jan. 2007.

Porowska et al., Composition of polifungin, a new antifungal agent, Rec. Trav. Chem., 91:780-784, 1971.

Ramirez F. et al., Differential effects on energy transduction processes by fluorescamine derivatives in rat liver mitochondria, Biochem. 19(9):1928-1933, 1980.

Sanglard D. Resistance of human fungal pathogens to antifungal drugs, Curr. Opinion Microbiol., 5:379-385, 2002.

Schaffner et al., Biologically active N-Acyl derivatives of polyene macrolide antifungal antibiotics, Antibiot. Chemother., 11(11):724-732, 1961.

Schaffner, Chapter 12. Polyene macrolides in clinical practice: pharmacology and adverse and other effects, in Macrolide Antibiotics: Chemistry, Biology, and Practice, Academic Press. Inc., Orlando, pp. 457-507, 1984.

Schaffner et al., Polyene macrolide derivatives. I: N-acylation and esterification preactions with amphotericin B, J. Antibiot., 25(4):256-258, Apr. 1972.

Semis R. et al., Activity of an intralipid formulation of nystatin in murine systemic candidiasis, J. Antimicr. Ag., 38:336-340, 2011.

Semis R. et al., Phamacokinetics, tissue distribution and immunomodulatory effect of intralipid formulation of nystatin in mice, J. Antimicrob. Chemother., 67:1716-1721, 2012.

Semis R. et al., Mechanism of activity and toxicity of nystatin-intralipid, Med. Mycol., 51:422-431, May 2013.

Semis R. et al., Nystatin-intralipid preparation: characterization and in vitro activity against yeasts and molds, Mycopathologia, 169:333-241, 2010.

Silva L. et al., Solution conformation of a nitrobenzoxadiazole derivative of the polyene antibiotic nystatin: a FRET study, J. Photochem. Photobiol. B. Biol., 72:17-26, 2003.

Singh N., Invasive aspergillosis in organ transplant recipients: new issues in epidemiologic characteristics, diagnosis, and management, Med. Mycol. Suppl 1, 43:S267-S270, 2005.

Ślisz et al., Studies of the effects of antifungal cationic derivatives of amphotericin B on human erythrocytes, J Antibiot., 57(10):669-678, Oct. 2004.

Ślisz et al., The mechanism of overcoming multidrug resistance (MDR) of fungi by amphotericin B and its derivatives, J Antibiot., 60(7):436-446, 2007.

Soloviera S. E. et al., Chemical modification of antifungal polyene macrolide antibiotics, Rus. Chem. Rev. 80(2):103-126, 2011.

Sowinski P. et al., The structure of amphotericin A: II. The complete structure of the antibiotic, J. Antibiot., 38(2)175-180, Feb. 1985.

Stefanska B. et al. A new method of preparation of polyene macrolide antibiotics esters, Acta Poloniae Pharmaceutica. 40(2): 171-174, 1983.

Stefańska B. et al., Enamine and amidine derivatives of polyene macrolide antibiotics, Acta Polon. Pharm., XLV(1):71-76, 1988.

Thomas A. H. et al., The heterogeneous composition of pharmaceutical-grade nystatin, The Analyst, 107(1277):849-854, Aug. 1982.

Thomas A. H. et al., Identification and determination of the qualitative composition of nystatin using thin-layer chromatography and high-performance liquid chromatography, J. Chemother., 216:367-373, 1981.

Tsao S. et al., Relative contributions of the candida albicans ABC transporters Cdr1p and Cdr2p to clinical azole resistance, Antimicrobial Agents and Chemotherapy, 53(4):1344-1352, Apr. 2009.

Wakiec R. et al., Voriconazole and multidrug resistance in candida albicans, Mycoses, 50:109-115, 2007.

Yu et al., Organofluorine derivatives of nystatin, Pharmac. J., 32(2):109-110, 1998.

Zerbib C. et al. One-pot synthesis of a new antifungal polymerisable monomer and its characterization by coordination-ion spray mass spectrometry, Rapid Comm. in Mass Spec. 25(15):2141-2148, 2011.

Zieliński J. et al., The structure of a novel sugar component of polyene macrolide antibiotics: 2,6-dideoxy-L-ribohexopyranose, J. Antibiot., 32(6):565-568, Jun. 1979.

Zieliński J. et al., The structure of nystatin $A_3$, a component of nystatin complex, J. Antibiot., 41(9):1289-1291, Sep. 1988.

(56) References Cited

OTHER PUBLICATIONS

Baginski et al., Apr. 1, 1994, The role of amphotericin B amine group basicity in its antifungal action. A theoretical approach, Biophysical Chemistry, 49(3):241-250.
Volmer et al., Jan. 1, 2010, Synthesis and biological evaluation of amphotericin B derivatives, Natural Product Reports, 27(9):1329.
Szlinder-Richert et al., Apr. 1, 2004, Interaction of amphotericin B and its low toxic derivative, N-methyl-N-D-fructosyl amphotericin B methyl ester, with funfal, mammalian and bacterial cells measured by the energy transfer method, Il Farmaco, 59(4):289-296.
International Search Report and Written Opinion dated Aug. 26, 2013 in PCT/EP2013/054621.
Milewska, Maria J. et al., N-substituted derivatives of nystatin of improved selective toxicity are active against multidrug-resistant yeast, Sep. 23-27, 2010, p. 61; P13, 28$^{th}$ Small Meeting on Yeast Transport and Energetics:(SMYTE), Abstract Book Poster Session, New Delhi, India.
The Patent Office of the Republic of Poland, Search Report, Jul. 31, 2012, Warszawa, Poland.
The Patent Office of the Republic of Poland, Search Report, Oct. 18, 2012, Warszawa, Poland.
Belakhov et al., Synthesis and antifungal activity of N-benzyl derivatives of Amphotericin B, *Pharmaceutical Chemistry Journal*, 41(7)362-366, 2007.
Wydro et al., Interactions of Amphotericin B derivative of low toxicity with biological membrane components—the Langmuir monolayer approach, *Biophysical Chemistry*, 116:77-88, 2005.
Examination Report No. 1 dated Dec. 16, 2016 in Australian Application No. 2013276480.

\* cited by examiner

N-SUBSTITUTED SECOND GENERATION DERIVATIVES OF ANTIFUNGAL ANTIBIOTIC AMPHOTERICIN B AND METHODS OF THEIR PREPARATION AND APPLICATION

The subject of the invention concerns the new N-substituted derivatives of polyene macrolide antifungal antibiotic Amphotericin B, called the second generation modification products. They are characterized by the presence of bulky moieties at the substituent linked to amino group of the antibiotic, inducing steric hindrance effect, also esters and amides of such derivatives and their salts with acids or bases or products containing complexing compounds, as water soluble forms. Also presented are methods for obtaining the compounds, according to the invention, and their use in the preparation of antifungal drugs for medical and veterinary needs and for plant protection, as well as for other applications, like protection of buildings from fungal infections.

BACKGROUND TO THE INVENTION

Chemotherapy of fungal infections is one of the most difficult and not yet successfully solved problems in modern medicine. This is a consequence of the fact that both, pathogenic fungal organisms, and the humans are eukaryotic organisms and this is the reason of essential difficulties in designing of the selectively acting drugs with low toxicity for the patient. This difficulty has been omitted only in the treatment of topical and intestinal fungal infections. This includes such areas of clinical mycology as gynecology, dermatology, gastroenterology, pulmomology, urology and ophthalmology, where the problem of compounds toxicity occurs to be less dramatic (C. P. Schaffner, in Macrolide antibiotics, S. Omura (red.), Academic Press. Inc., Orlando, p. 457, 1984). The most popular drugs of polyene macrolides used in such cases are Amphotericin B, Nystatin and Pimaricin, which due to the lack of resorption in local and oral administration are practically non-toxic. However, invasive mycoses concerning the infection of internal organs and fungemia are still problems far from successful solution. Current epidemiological statistics concerning the mortality in such types of illnesses are not satisfactory (M. A. Pfaller, D. J. Diekem, Clin. Microbiol. Rev. 20, 133, 2007; T. F. Patterson, Lancet 366, 1013, 2005; S. K Fridkin, Clin. Infect. Dis. 41, 240, 2005). Especially dangerous are invasive candidoses and aspergilloses and infections caused by certain others fungal pathogenes. In the case of invasive candidosis the mortality is in the range 30-70%, aspergillosis more than 50%, the frequency of invasive mycoses in oncology/hematology is approximately 50%, in the case of mycoses of children with leukemia is 29-39% (S. E. Soloviera et al., Rus. Chem. Rev. 80, 103, 2011: A. L. Demain, S. Sanchez, J. Antibiot., 62, 5, 2009; G. O. Bronin et al., Pediatryia 4, 31, 2004). Over 90% of HIV-positive patients suffer from mycoses, and pneumonia caused by *Pneumocystis carinii* which is the main reason of death in patients with AIDS. Systemic mycoses are common reason of death in adult patients with leukemia. *Candida* spp., in regard to frequency of incidences, are fourth etiological factor of hospital infections and is a cause of 8-11% of all systemic infections with mortality up to 40%. The frequency of fungal infections in patients after organ transplants is in the range 5-40% depending on the type of transplanted organ. Invasive aspergillosis of lungs is a main reason of patient death after transplant of bone marrow. Blastomycosis, histoplasmosis and coccidiomycosis are endemic mycoses with high frequency of appearance in many regions of the world.

The unfavorable situation in clinical mycology for over 20 years constantly is getting worse for several reasons. One of them is steady increase of infections caused by fungal species previously being non-pathogenic (D. A. Enoch et al., J. Med. Microbiol. 55, 809, 2006; N. Nucii, K. A. Man, Clin. Infect Dis. 41, 521, 2005). The increase of fungal infections is also caused by the use of antibacterial chemotherapeutical agents with broad spectrum and by the use of steroids, and above all by decreasing the immune system activity in increasing number of patients as a consequence of the development of transplantology who required the use of immunosuppressive drugs, and also with the increase of cancer cases and thus usage of immunosuppressive cytostatics (N. Siugh, Med. Mycol. 43, suppl. 1, 267, 2005; A. L. Demain, S. Sanchez, J. Antibiot. 62, 5, 2009).

Especially worrying is the steady decrease of utility of currently clinically available antifungal chemotherapeutics used in the treatment of systemic infections. It is the result of rapid development of resistance of pathogenic fungal strains, above all the multidrug resistant (MDR) ones. The latter phenomenon is a consequence of overexpression of membrane transporter proteins of ABC and MFS superfamilies exporting from the microbial cells xenobiotics as antifungal chemotherapeutic agents (D. Sanglard, Curr. Opinion Microbiol. 5, 378, 2002; M. B. Frosco, J. F. Barrett, Exp. Opin. Invest. Drugs 7, 175, 1998; D. P. Kontoyiannis, R. E. Lewis, Lancet 359, 1135, 2002).

5-fluorocytosine, often used in combination with Amphotericin B to increase its uptake by membrane permeabilisation, as an antimetabolite avoids the exporting activity of MDR transporting proteins, but enhances the development of specific type of resistance mainly by the loss of cytosine permease and cytosine deaminase, which generates in cells the active metabolite—5-fluorouracil. Particularly clinically valuable fungicides of "azoles" group, mostly triazoles, such as myconazol, voriconazol, posaconazol and others, are partially susceptible to their removal from the cells by MDR exporting proteins (R. Franz et al., Antimicrob. Ag. Chemother., 42, 3065, 1998; R. Wakiec et al., Mycoses, 50, 109, 2007). However, being the inhibitors of lanosterol demethylase, interacting with the enzyme, induces changes in the structure of enzymatic protein leading to the loss of inhibitory activity of these compounds. Very valuable and very promising fungicide caspofungin, although with narrow antifungal spectrum but with excellent selectivity, as inhibitor of β-D-glucan synthase interacts with the enzyme, which unfortunately leads to the induction of changes in the structure of the enzyme protein and in consequence the loss of inhibitory activity of the compounds. The reports on growing resistance to the action of this drug start to be published. Therefore, Amphotericin B (fungizone)—from polyene macrolides group practically remains the only one systemic fungicide, which does not induce the development of resistant strains, and not being the substrate of MDR exporting proteins, retains full activity against multidrug resistant strains (M. Slisz i in., J Antibiot. 60, 436, 2007). Although there are data on the appearance of strains with reduced sensitivity to this antibiotic, as a result of certain changes in the lipid composition of cytoplasmic membrane, but these changes are phenotypic and regressing after discontinued contact with the drug. Moreover, Amphotericin B fulfills also other important requirements for a good antifungal chemotherapeutic such as high activity, broad antifungal spectrum and fungicidal action.

The present situation in clinical mycology points to the necessity for further searches of antifungal drugs. One of the intensively developing research projects concerned study on the modifications of Amphotericin B, aimed at removing of its main shortcomings which are high toxicity and lack of water solubility. However, until now none of the products of antibiotic modification have been introduced to clinical practice. The only practical progress in this area was the introduction to clinical use of Amphotericin B complexes with lipids or liposomal formulations as Abalcet®, Amphotec® and AmBisome®. These formulations of Amphotericin B are however only a little less toxic in comparison to the native antibiotic.

Earlier known derivatives of Amphotericin B are compounds modified mainly at amino group of mycosamine moiety and at carboxyl group of aglycone. The attempts to modify compounds by genetic manipulations of antibiotic producing organism have been also performed. These modifications have been intended to improve the solubility and to reduce the toxicity of the compound. Some of the obtained derivatives had better water solubility due to the introduction of hydrophilic substituents, or by the introduction to the molecules of moieties defining the ionic character of compounds which allows soluble salts to form. However, no significant progress has been achieved in improving the selective toxicity of Amphotericin B derivatives, because no convincing molecular background for the rational modifications has been proposed. The syntheses of derivatives had accidental character and were rather based on random screening.

The prior art on Amphotericin B derivatives includes: 1) derivatives at amino group, 2) derivatives at carboxyl group, 3) double derivatives including the modification of both amino and carboxyl groups, 4) derivatives with genetically modified aglycone fragment. Summary of the current state of knowledge on this matter is presented in the published scientific reviews (A. A. Volmer et al., Nat. Prod. Rep 27, 1329, 2010; S. E. Solovieva et al., Russian Chemical Reviews 80, 103, 2011). In the below mentioned survey of prior art the patent literature is also presented.

The first obtained are Amphotericin B derivatives at amino group. These are N-acyl derivatives (U.S. Pat. No. 3,244,590). An important improvement in this group of compounds deals with N-aminoacyl derivatives of high biological antifungal activity (J. K. Wright et al., J. Antibiol. 35, 911, 1982). There are also known their N,N-dialkylaminoacyl analogs more advantageous as concerns the method of their synthesis (PL 14847). Numerous further compounds were obtained in the group of derivatives at amino and carboxyl functions. A major advancement in the antibiotic modification was the use of N-alkylation reaction. N,N,N-trimethylammonium derivatives (U.S. Pat. No. 4,144,328; Polish Patent 122884), N-alkyl derivatives being products of Michael's addition (A. Czerwinski et al., J. Antibiol. 44, 979, 1991), derivatives being the products of Amadori rearrangement (Polish Patent 82224; U.S. Pat. No. 4,195,172) together with further modifications of glycosyl moiety (U.S. Pat. No. 5,314,999; L. Saint-Julien et al., Antimicrob. Agents Chemother. 36, 2722, 1992) have been obtained. This type of derivatives were further modified as derivatives at amino and carboxyl groups jointly. Major progress in the synthesis of Amphotericin B N-alkyl derivatives was the application of reductive amination reaction with the use of appropriate aldehydes (V. Paquet, E. M. Carreira, Organic Letters 8, 1807, 2006; Europ. Patent Application. EP 1987049A1; International Patent Application WO 2007096137A1; US Patent Application 2009/0186838A1).

Also other derivatives, less interesting as regards their properties, such as guanidine derivative (U.S. Pat. No. 4,396,619) and amidine and enamine derivatives (Polish Patent 120111) have been obtained.

Much fewer derivatives at carboxyl group have been obtained. The first compound of this type which caused a great interest was methyl ester of Amphotericin B (U.S. Pat. No. 4,035,567) and a number of its water soluble salts (U.S. Pat. Nos. 3,914,409; 6,613,889B2; 4,041,232; Patent Application PCT WO 2007/06335A2). Also other esters of the antibiotic and their salts were obtained (U.S. Pat. No. 5,981,729; S. Stefanska et al., Acta Polon. Pharm. 40, 1, 1983), other derivatives at carboxyl group comprised hydrazides (K. Grzybowska, E. Borowski, J. Antibiot. 43, 907, 1990), (PL 122086; PL 199213) and their water soluble salts (Polish Patent 138831).

A large group of Amphotericin B derivatives are compounds in which a number of the above mentioned substituents at amino and carboxyl groups were combined in one compound. There are amides and esters of N,N-dialkyl derivatives (WO 2009/0186838A1; WO 2007/096137A1), esters and amides of glycosyl derivatives and their N-alkyl derivatives (U.S. Pat. Nos. 6,562,796B2; 6,664,241B2), amides and esters of N-alkyl and N-aminoacyl derivatives (PL 199213), methyl esters of N-alkyl N-glycosyl derivatives (PL 180253), esters of guanidine derivatives (U.S. Pat. No. 4,396,610), methyl ester of N-amino and amidine derivatives (PL 120035), esters and amides of dialkylaminoacyl derivative (PL 142848).

Separate group of products of Amphotericin B modifications constitute compounds and their various derivatives with modified macrolide part of the antibiotic molecule. These compounds are not relevant to the subject matter of the present invention, which relates to Amphotericin B derivatives with unmodified macrolide ring, but for the sake of the complete information on prior art, relevant patents and patent applications are mentioned. Beecham group documents include: (U.S. Pat. Nos. 6,284,736; 5,116,960; 5,066,646; 5,100,876; EP 0350164; WO 91/09047; EP 0431870; EP 0375222; EP 0431870. Smith-Kline Beecham group documents include: WO 93/16090; WO 93/14100; WO 93/17034.

Above presented the state of prior art allows to put forward the following conclusion. In spite of a large experimental data and a very large number of Amphotericin B derivatives obtained, none of these compounds have yet entered the stage of advanced clinical trials and industrial development, because the essential improvement of their properties in relation to the native antibiotic was not achieved.

The background of the invention is the new idea which enables the Amphotericin B modification, aimed to obtain the most desired effect which is essential increase of selective toxicity of antibiotic derivatives. Our study has shown that selective toxicity of Amphotericin B derivatives is only to the limited extent the result of differential affinity of derivatives to their molecular targets in fungal (ergosterol) and mammalian (cholesterol) cells indispensable for the creation of lethal channels (M. Baginski et al., Bichim. Biophys. Acta 1567, 223, 2002). Differences of that affinity cannot by essentially increased by the chemical modification of the antibiotic and thus some changes in the affinity to both molecular targets can give rather limited increase of selective toxicity effect of the modified compounds. We suggest that the derivatives of Amphotericin B with somewhat modified differential affinity to cholesterol and ergosterol, should be named derivatives of the first generation. Much more possibility for the essential increase of selective toxicity of Amphotericin B derivatives gives, observed by us, phenomenon of differential ability to create lethal channels in fungal and mammalian cells not only as a result of differences of compounds affinity to molecular targets in both types of organisms but above all as a result of differential ability of formed antibiotic—molecular target complex to aggregate leading to the formation of a lethal membrane channels. This occurs in the case of N-substituted antibiotic derivatives containing voluminous or bulky moieties which can induce steric hindrance effect (J. Szlinder-Rychert et al., Biochem. Biophys. Acta 1528, 15, 2001; J. Szlinder-Rychert et al., Il Farmaco 59, 289, 2004). It is possible, that Amphotericin B derivatives with bulky substituents at amino group, form antibiotic-sterol complexes with modified geometry and thus result in the differential ability to aggregate into lethal membrane channels with ergosterol and cholesterol containing membranes. It is also important, that spatially hindered compounds retain their high activity towards fungal strains with multidrug resistance (M. Slisz et al., J. Antibiot. 60, 436, 2007). Such type of antibiotic derivatives we call the derivatives of second generation. In contrast to the derivatives at amino group, the spatially hindered derivatives at carboxyl group do not give the essential improvement of selectivity effect. The basic derivatives such as esters and amides can only augment the advantageous properties of spatially hindrance N-derivatives, facilitating the formation of soluble salts with acids. Amphoteric derivatives can form soluble salts with bases, because bulky N-substituents break the zwitterionic structure of the native antibiotic.

The advantage of new semisynthetic Amphotericin B derivatives, according to the invention, is that they exhibit high antifungal activity against a broad spectrum of microorganism of the *Candida* species and filamentous fungi, as well as towards multidrug resistant (MDR) strains with overexpression of transporter protein Cdr1p and Cdr2p. These derivatives also exhibit low hemotoxicity, which is essential factor of toxicity of polyene macrolides, and form water soluble salts.

Unexpected novelty permitting to obtain, according to the invention, advantageous effect of hemotoxicity reduction, is introduction to the substituents at amino group of Amphotericin B of new appropriate bulky moieties, which may induce the steric hindrance effect. It appeared that such steric hindrance factor decreases lethal permeabilising activity of Amphotericin B derivatives at greater degree towards mammalian than fungal cells, what increases their selectivity of action and essentially reduces hemotoxity of these compounds. Bulky moieties which may give the optimal effect of steric hindrance include ring systems carbo-, as well as heterocyclic, alicyclic and aromatic, bulky substituents as tert-butyl, nitro group, bromine atom and also aliphatic moieties which due to their flexibility can form voluminous conformational structures.

SUMMARY OF INVENTION

Accordingly, in a first aspect, the invention provides sterically hindered N-substituted derivatives of antifungal antibiotic Amphotericin B according to the Formula 1a:

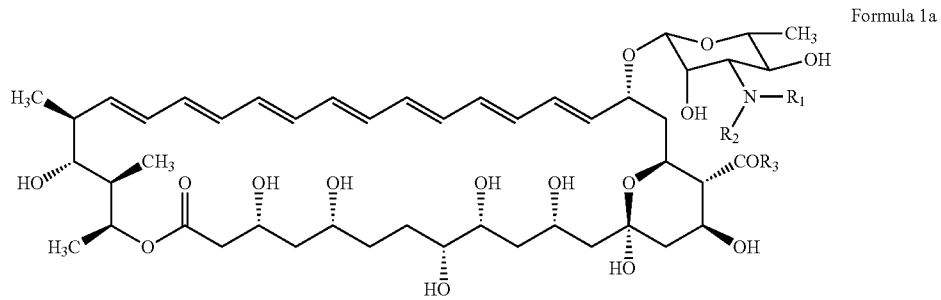

Formula 1a

The beneficial effect for the increase of selective toxicity of the introduction of steric hindrance at amino group of mycosamine moiety of the antibiotic molecule is achieved, providing that the basic character of amino group is preserved (N-alkyl derivatives), or as a new amino group is present in the substituent (N-aminoacyl derivatives). The particularly important role of this group in the interaction with sterole molecular targets has been evidenced (M. Baginski et al., Biophys. Chem. 49, 241, 1994). Discussed above idea on the positive effect of spatially hindered N-substituted Amphotericin B derivatives does not allow to identify the exact molecular structures which should have the compounds with optimal properties. Synthesis and selection of the most favorable compounds is still a matter of empiricism. The first group of such derivatives was obtained (PL 210774). However further empirical studies were needed for the identification of the most favorable compounds. This aim has been achieved within the present invention, as a result of unexpected identification of sterically hindered derivatives with most advantageous selectivity.

or a salt, hydrate or complex thereof;
wherein $R_1$ is chosen from a hydrogen atom, optionally substituted alkyl, a succinimidyl derivative, a glycosyl residue, an optionally substituted aminoacyl residue, or an optionally substituted thioureidyl residue;
$R_2$ is a hydrogen atom or a substituent such as defined for $R_1$;
$R_3$ is a hydroxyl group, alkoxyl group or an alkylamino or aminoalkyl derivative.

In certain embodiments, $R_1$ and $R_2$ are not both hydrogen. Classes and subclasses of N-substituted derivative compounds of Formula 1a are described further herein.

DEFINITIONS

The term "halogen" or "halo" as used herein means fluorine, chlorine, bromine or iodine.
The term "heteroatom" as used herein refers to one or more of oxygen, sulfur, nitrogen, phosphorus or silicon.
The term "aliphatic" as used herein refers to a straight or branched chain hydrocarbon which is completely saturated or contains one or more units of unsaturation. Thus, aliphatic may be alkyl, alkenyl or alkynyl, preferably having up to 20 carbon atoms, up to 12 carbon atoms or up to 6 carbon atoms.

The terms "bulky", "spatially expanded", "spatially hindered" of "voluminous", which can be used interchangeably, as used herein refer to a group or moiety which may give the effect of steric hindrance and includes ring systems carbo-, as well as heterocyclic, alicyclic and aromatic, bulky substituents such as tert-butyl, nitro group, bromine or iodine atoms and also aliphatic fragments, which, due to their flexibility, can form voluminous conformational structures. In the context of the invention a bulky alkyl may, for example be optionally substituted branched alkyl of 4 or more carbon atoms or an optionally substituted alkyl or alkyl-comprising moiety, also comprising an optionally substituted carbo- or heterocyclic, aminoacyl, thioureidyl or succinimdyl moiety.

The term "alkyl" as used herein refers to a straight or branched chain alkyl group. Preferably, an alkyl group as referred to herein is a $C_1$-$C_{20}$alkyl group, preferably a $C_1$-$C_{12}$alkyl group. More preferably, an alkyl group as referred to herein is a lower alkyl having 1 to 6 carbon atoms.

The term "non-branched", used interchangebly with "simple", as used herein refers to a straight chain alkyl group. Preferably, a simple alkyl group as referred to herein is a lower alkyl having 1 to 6 carbon atoms.

The terms "carbocycle" or "carbocyclic moiety" as used herein refer to a saturated or partially unsaturated mono-, bi- or tri-cyclic group having 3 to 14, preferably 3 to 8 and more preferably 3 to 6, ring carbon atoms or a mono-, bi- or tri-cyclic aromatic ring having 6 to 14, preferably 6 to 10, carbon atoms. A carbocycle is a cycloaliphatic, preferably a "cycloalkyl" which as used herein refers to a fully saturated hydrocarbon cyclic group, or an "aryl". Preferably, a cycloalkyl group is a $C_3$-$C_6$ cycloalkyl group and preferably, an aryl is phenyl or napthyl. Bi- or tri-cyclic groups may contain fused aromatic, saturated and/or partially unsaturated rings.

The terms "heterocycle" or "heterocyclic moiety" as used herein refer to a saturated or partially unsaturated mono-, bi- or tri-cyclic group having 3 to 14, preferably 3 to 10, ring atoms or a mono-, bi- or tri-cyclic aromatic ring having 6 to 14, preferably 6 to 10, ring atoms and having, in addition to carbon ring atoms, one or more ring heteroatoms selected from O, N, P and S (preferably O, N and S). A heterocycle is cycloheteroaliphatic, preferably a "heterocycloalkyl", which as used herein refers to a saturated heterocyclic group, or a "heteroaryl", which refers to a monocyclic or bicyclic aromatic ring system. A heterocycle preferably has 3 to 7 ring atoms or if aromatic, 5 to 10 ring atoms and may contain fused aromatic, saturated and/or partially unsaturated rings. Preferably a heterocycle is piperidine, morpholine, piperazine, pyrrolidine, pyridine or imidazole.

An aliphatic, alkyl, carbocycle, heterocycle, cycloalkyl, aryl, heteroaryl or aminoacyl group as referred to in respect or any of the chemical moeities described herein, may be unsubstituted or may be substituted by one or more substituents independently selected from the group consisting of halo, aliphatic, —OR°, —R°, —SR°, NHR°, —NR°$_2$, —COR°, —COOR°, —NH$_2$, —NO$_2$, —OH, —COOH, —CN, hydroxyalkyl, alkylcarbonyloxy, alkoxycarbonyl, alkylcarbonyl or alkylsulfonylamino, wherein R° is an optionally substituted aliphatic (preferably alkyl), carbocycle (preferably aryl or cycloalkyl) or heterocycle (preferably heteroaryl or heterocycloalkyl) optionally substituted with or with any one or more of substituents independently selected from halo, aliphatic, —OR, —R, —SR, NHR, —NR$_2$, —COR, —COOOR, —NH$_2$, —NO$_2$, —OH, —COOH, —CN, hydroxyalkyl, alkylcarbonyloxy, alkoxycarbonyl, alkylcarbonyl or alkylsulfonylamino, wherein R is as defined for R°, substituted or unsubstituted. Preferred substituents include halo, lower alkyl, alkylamino, —NH$_2$, NO$_2$, —OH, —CN, alkoxy or alkoxycarbonyl. Most preferred substituents include tert-butyl, —NO$_2$ and bromine.

An alkylamino or aminoalkyl derivative is a moiety comprising an alkylamino or an aminoalkyl moiety, the alkyl portion of which may be optionally substituted with any substituent as described for alkyl above.

The term "alkylamino" as used herein includes "monoalkylamino" and "dialkylamino", i.e. —NH(alkyl) and —N(alkyl)$_2$.

The term "succinimidyl derivative" as used herein refers to a moiety containing a succinimide residue of structure

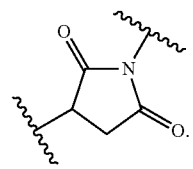 [SMILES: *C1CC(=O)N(*)C1=O]

Preferably, a succinimidyl derviative is of structure

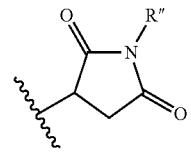

wherein R" is an optionally substituted aliphatic or an optionally substituted carbo- or heterocyclic moiety.

The term "glycosyl" as used herein refers to a cyclic monosaccharide or oligosaccharide. Preferably, glycosyl is fructosyl.

The term "thioureidyl residue" as used herein refers to a substituent bonded to a nitrogen atom to form a —N—C (S)—NR'$_2$ group, wherein each R' is independently selected from a hydrogen atom or R" as defined above. Preferably R' is a hydrogen atom or an optionally substituted aliphatic and more preferably one R' is a hydrogen atom and the other R' is an optionally substituted aliphatic.

The term "ester" refers to a group —C(O)O—R, wherein R is, for example, optionally substituted aliphatic, carbocycle or heterocycle.

The term "alkoxy" as used herein refers to a group of the form —O—R, wherein R is alkyl, preferably lower alkyl.

The term "alkylthio moiety" as used herein refers to a group of the form —S—R, wherein R is alkyl, preferably lower alkyl.

The term "aminoacyl residue" refers to a moeity comprising an optionally substituted aminoacyl group, wherein an aminoacyl group as used herein refers to an acyl group substituted with an amine, monoalkylamine or dialkylamine at the α- or β-position relative to the carbonyl. Aminoacyl may be substituted by one or more substituents as described above. In some embodiments, aminoacyl may be substituted by one or more substituents independently selected from the group consisting of optionally substituted aliphatic, alkoxy, aralkyl, heteroaralkyl, carbocyclo, heterocyclo, alkylcarbonyloxy, alkoxycarbonyl or alkylcarbonyl. Preferred substituents include optionally substituted lower alkyl, alkylamino (monoalkylamino or dialkylamino), aralkyl, heteroaralkyl, carbocyclo and heterocyclo.

The terms "aralkyl" and "heteroaralkyl" as used herein refers to an alkyl group as defined above substituted with an aryl or heteroaryl group as defined above. The alkyl component of an "aralkyl" or "heteroaralkyl" group may be substituted with any one or more of the substituents listed above for an aliphatic group and the aryl or heteroaryl component of an "aralkyl" or "heteroaralkyl" group may be substituted with any one or more of the substituents listed above for aryl, heteroaryl, carbocycle or heterocycle groups. Preferably, aralkyl is benzyl.

concentration of at least 10 mg/ml, preferably at least 20 mg/ml. As described herein, a compound of the invention may also be provided in the form of a complex, with a complexing agent. In the context of the invention, a complex may be considered to be water soluble if it forms a transparent colloidal suspension in water, for example under the conditions mentioned above.

The term "complexing compound" as used herein refers to a compound with which a compound of the invention can form a non-covalent complex. Complexing compounds can include, for example, calcium salts, succinic acid, sodium deoxycholate or sterols.

DETAILED DESCRIPTION OF INVENTION

In a first aspect, the invention provides sterically hindered N-substituted derivatives of Amphotericin B. Accordingly, the invention provides a compound according to the Formula 1a:

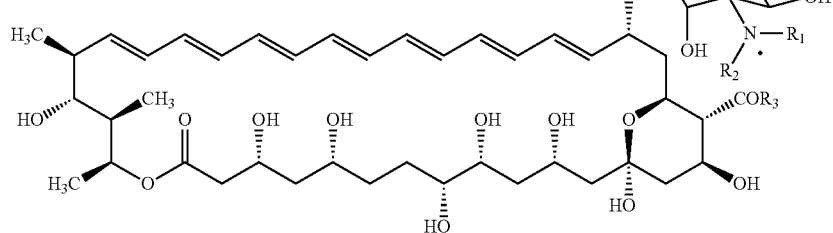

Formula 1a

In compounds of the invention, one or more asymmetric carbon atoms may be present. For such compounds, the invention is understood to include all isomeric forms (e.g. enantiomers and diastereoisomers) of the compounds as well as mixtures thereof, for example racemic mixtures.

A compound of the invention, including salts, hydrates and complexes thereof, may in some embodiments be provided in a water soluble form. A compound can be considered to be water soluble, for example, if it will dissolve in water at room temperature (20° C.), optionally with heating, agitation or sonication. In some embodiments, a compound of the invention (e.g. in a salt form) may be considered water soluble if it is soluble in water at room temperature at a or a salt, hydrate or complex thereof;

wherein $R_1$ is chosen from a hydrogen atom, optionally substituted alkyl (preferably a non-branched alkyl or a substituted alkyl), a succinimidyl derivative, a glycosyl residue, an optionally substituted aminoacyl residue, or an optionally substituted thioureidyl residue;

$R_2$ is a hydrogen atom or a substituent such as defined for $R_1$;

$R_3$ is a hydroxyl group, alkoxy group or an alkylamino or aminoalkyl derivative;

wherein $R_1$ and $R_2$ are not both a hydrogen atom.

In some embodiments a compound of Formula 1a as defined above may be a compound according to Formula 1b:

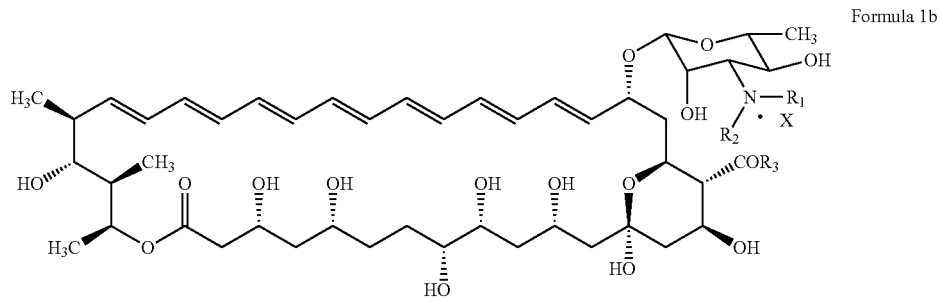

Formula 1b wherein $R_1$, $R_2$ and $R_3$ are as defined in respect of formula 1a;

X is absent or present and, when present, X is one or more molecules of base or acid, or complexing compound.

In some embodiments a compound of the invention is a compound according to Formula 1:

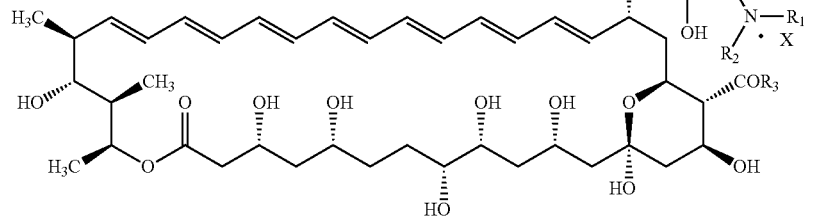

Formula 1 wherein $R_1$ is chosen from a hydrogen atom, a non-branched alkyl with 1 to 15 carbon atoms, a spatially extended alkyl with 1 to 15 carbon atoms, including a succinimidyl derivative, an alkyl derivative containing cyclic carbo- or heterocyclic ring moieties with 5 to 8 atoms, a glycosyl residue, an optionally substituted or spatially branched aminoacyl residue, a dialkylaminoacyl residue with 1 to 5 of carbon atoms in the alkyl substituent, a thioureidyl residue optionally substituted with a bulky aliphatic or cyclic substituent containing at least one basic nitrogen atom;

$R_2$ is hydrogen atom or substituents as defined for $R_1$;

$R_3$ is hydroxyl group, alkoxy or an aminoalkyl derivative; and its water-soluble salts and complexes, where X is one or more molecule of base acid or complexing compound.

In further embodiments, the invention provides a compound of formula 1a, 1b or 1, wherein one or both of $R_1$ or $R_2$ (preferably one) is a bulky substituent, represented by an optionally substituted thioureidyl residue, substituted alkyl, a succinimidyl derivative, a glycosyl residue, or an optionally substituted aminoacyl residue, for example of the structure as defined in respect of any of sub-classes (a) to (f) below:

(a) In some embodiments, the invention provides a compound wherein one or both (preferably one) of $R_1$ or $R_2$ is a thioureidyl residue of structure

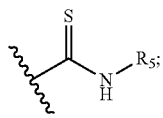

and wherein $R_5$ is —W—Z, wherein W is an optionally substituted alkyl linker or a single bond; and Z is an optionally substituted carbocycle or heterocycle (preferably aryl, heteroaryl or nitrogen-containing heterocycloaliphatic (preferably N-linked heterocycloalkyl)), or $NR^*_2$, $NH_2$, $NHR^*$, where $R^*$ is an optionally substituted aliphatic (preferably lower alkyl), an optionally substituted carbo- or heterocyclic moiety, or two $R^*$ form, together with the nitrogen atom to which they are bound, an optionally substituted heterocycle. W may be a single bond, branched or non-branched alkyl, e.g. lower alkyl. In some embodiments, Z is unsubstituted or substituted with one or more of alkyl or halo. Preferably Z is phenyl, piperidinyl, morpholinyl, pyrrolidinyl, pyridinyl or alkylamino, all of which may be substituted.

(b) In some embodiments, the invention provides a compound wherein one or both of $R_1$ and $R_2$ is -alkyl (for example, $C_{1-6}$alkyl, $C_{2-6}$alkyl, or $C_{3-6}$alkyl) substituted with an optionally substituted alkylamino or an optionally substituted carbo- or heterocyclic moiety. In some embodiments, one or both of $R_1$ and $R_2$ is, independently, -alkyl (for example $C_{1-6}$alkyl, preferably $C_{2-6}$alkyl, more preferably $C_{3-6}$alkyl, $C_3$alkyl or $C_4$alkyl) substituted with a dialkylamino or an optionally substituted N-containing heterocycle (preferably heterocycloalkyl and more preferably piperidinyl or piperazinyl). In some embodiments, the heterocycle is N-linked and is unsubstituted or substituted with alkyl. In some other embodiments, one or both of $R_1$ or $R_2$ (preferably one) is alkyl (for example $C_{1-6}$alkyl, preferably $C_{1-3}$alkyl, more preferably $C_1$alkyl) substituted with an optionally substituted carbocycle (preferably aryl), wherein the carbocycle, when substituted, is preferably substituted with one or more substituents selected from optionally substituted carbocycle or heterocycle, aliphatic (preferably branched $C_{3-6}$alkyl), alkylamino, alkoxy nitro, halo (preferably bromo), or alkoxycarbonyl. In some embodiments one of $R_1$ or $R_2$ is an optionally substituted benzyl group. Optionally substituted benzyl may preferably be substituted with one or more substituents selected from optionally substituted carbocycle or heterocycle, aliphatic (preferably branched $C_{3-6}$alkyl), alkylamino, alkoxy nitro, halo (preferably bromo), or alkoxycarbonyl. In some embodiments, benzyl is substituted with alkylamino (preferably dialkylamino), carbocycle (for example aryl), or branched $C_{3-6}$alkyl (preferably tert-butyl, any of which may be optionally substituted.

(c) In some embodiments, the invention provides a compound wherein one or both (preferably one) of $R_1$ or $R_2$ is a succinimidyl derivative of structure

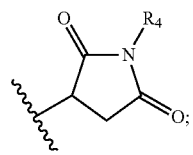

wherein $R_4$ is —X—Y, wherein X is an optionally substituted alkyl linker or a single bond; and Y is an optionally substituted carbo- or heterocyclic moiety or —OH, —OR*, —$NR^*_2$, —$NH_2$, —NHR*, where R* is an optionally substituted aliphatic, an optionally substituted carbo- or heterocyclic moiety or two R* form, together with the nitrogen atom to which they are bound, an optionally substituted heterocycle. X may be a single bond or a branched or non-branched alkyl, e.g. lower alkyl. Preferably, Y is an optionally substituted carbo- or heterocyclic moiety, hydroxyl or a dialkylamino. In some embodiments, $R_4$ is optionally substituted aryl (preferably phenyl), alkyl substituted with optionally substituted aryl (preferably benzyl), alkyl substituted with optionally substituted N-linked heterocycle or hydroxyl, or alkyl (preferably branched alkyl) substituted with alkylamino (preferably dialkylamino). In any of the above embodiments, where Y is a carbo- or heterocyclic moiety, Y is unsubstituted or substituted and in some embodiments Y may be substituted with one or more of alkyl (preferably non-branched lower alkyl, e.g. methyl or ethyl, or branched $C_{3-6}$alkyl, e.g. tert-butyl), nitro or halo (preferably bromo).

(d) In some embodiments, the invention provides a compound wherein one or both (preferably one) of $R_1$ or $R_2$ is an aminoacyl residue of structure:

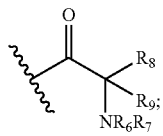

wherein $R_6$ and $R_7$ are independently chosen from a hydrogen atom or an optionally substituted alkyl (preferably lower alkyl), or $R_6$ and $R_7$ can be taken, together with the atom to which they are joined, to form an optionally substituted nitrogen-containing cyclic moiety; $R_8$ and $R_9$ are, independently, hydrogen or —U—V, wherein U is an optionally substituted alkyl linker (preferably lower alkyl and preferably unsubstituted) or a single bond and V is an optionally substituted aliphatic, carbocyclic (preferably aryl or napthyl), heterocyclic (preferably heteroaryl or heterocycloalkyl), alkoxy, alkylthio moiety, or ester moiety, any of which may be optionally substituted. In some embodiments, one of $R_8$ and $R_9$ is hydrogen. In some embodiments, one of $R_8$ and $R_9$ is hydrogen and the other of $R_8$ and $R_9$ is —U—V, wherein U is an optionally substituted alkyl linker (preferably lower alkyl) or a single bond and V is an optionally substituted carbo- or heterocycle (preferably aryl, for example phenyl or napthyl, heteroaryl or heterocycloalkyl), —$OR^{9a}$, —$SR^{9a}$ or —$C(O)OR^{9a}$, wherein $R^{9a}$ is optionally substituted branched alkyl (preferably $C_{3-6}$alkyl, for example tert-butyl) or optionally substituted carbo- or heterocycle and $R_6$ and $R_7$ are as defined above, preferably lower alkyl or hydrogen. In any of the above embodiments, where V is a carbo- or heterocyclic moiety, V may be unsubstituted or substituted, for example, with one or more of alkyl, nitro or halo.

(e) In some embodiments, the invention provides a compound wherein one or both (preferably one) of $R_1$ or $R_2$ is an aminoacyl of structure:

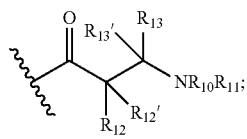

wherein; $R_{10}$ and $R_{11}$ independently chosen from a hydrogen atom or an optionally substituted alkyl or $R_{10}$ and $R_{11}$ can be taken, together with the atom to which they are joined, to form an optionally substituted nitrogen-containing cyclic moiety;

$R_{12}$ and $R_{13}$ are, independently, hydrogen or —U—V, wherein U is an optionally substituted alkyl linker or a single bond and V is a hydrogen atom, or an optionally substituted aliphatic, carbocyclic, heterocyclic, alkoxy, alkylthio moiety or ester moiety, any of which may be optionally substituted; and $R_{12'}$ and $R_{13'}$ are, independently, hydrogen or alkyl (preferably lower alkyl). Preferably V is a carbocyclic (preferably aryl or napthyl), heterocyclic (preferably heteroaryl or heterocycloalkyl), alkoxy, alkylthio moiety, or ester moiety, any of which may be optionally substituted. In some embodiments one of $R_{10}$ and $R_{11}$ is hydrogen and the other of $R_{10}$ and $R_{11}$ is —U—V, wherein U is an optionally substituted alkyl linker (preferably lower alkyl) or a single bond and V is an optionally substituted carbo- or heterocycle (preferably aryl, for example phenyl or napthyl, heteroaryl or heterocycloalkyl), —$OR^{9a}$, —$SR^{9a}$ or —$C(O)OR^{9a}$, wherein $R^{9a}$ is optionally substituted branched alkyl (preferably $C_{3-6}$alkyl, for example tert-butyl) or optionally substituted carbo- or heterocycle and $R_{12}$, $R_{12'}$, $R_{13}$ and $R_{13'}$ are as defined above, preferably lower alkyl or hydrogen. In any of the above embodiments, where V is a carbo- or heterocyclic moiety, V may be unsubstituted or substituted, for example, with one or more of alkyl, nitro or halo.

(f) In some embodiments, the invention provides a compound wherein one or both (preferably one) of $R_1$ or $R_2$ is a glycosyl residue, preferably a fructosyl residue (more preferably fructopyranose residue of structure

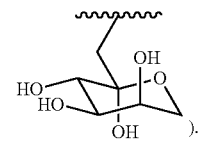

In some embodiments, wherein one of $R_1$ or $R_2$ is a glycosyl residue and the other of $R_1$ or $R_2$ is an unsubstituted alkyl or hydrogen, $R_3$ is hydroxyl. In some other embodiments, one of $R_1$ or $R_2$ is a glycosyl residue and the other of $R_1$ or $R_2$ is a substituted alkyl as defined in subclass (b), preferably an alkyl substituted with an optionally substituted alkylamino (preferably dialkylamino) or an optionally substituted heterocycle (preferably N-containing heterocycle, and more preferably N-linked heterocycloalkyl).

In some embodiments, one of $R_1$ or $R_2$ is as defined in respect of any of subclasses (a) to (f), preferably (a) to (d) and (f), and the other of $R_1$ or $R_2$ is hydrogen, unsubstituted alkyl (preferably non-branched), substituted alkyl or a substituent as defined in respect of any of subclasses (a) to (f).

In some embodiments, the invention provides a compound wherein one of $R_1$ and $R_2$ is a hydrogen atom or an unsubstituted alkyl (preferably non-branched) or a substituted alkyl (for example as defined in respect of subclass (b)); and the other of $R_1$ and $R_2$ is an unsubstituted non-branched alkyl, a substituted alkyl, or a succinimidyl derivative, a glycosyl residue, an optionally substituted aminoacyl residue, or an optionally substituted thioureidyl residue, preferably as defined in respect of any of subclasses (a) to (f). In some preferred embodiments, one of $R_1$ and $R_2$ is a hydrogen atom, a non-branched alkyl or alkyl substituted with alkylamino (preferably dialkylamino) or an optionally substituted carbo- or heterocyclic moiety (preferably a N-linked heterocycloalkyl, optionally substituted with alkyl); and the other of $R_1$ and $R_2$ is a substituted alkyl (preferably substituted with an optionally substituted carbo- or heterocyclic moiety), a succinimidyl derivative, a glycosyl residue, an optionally substituted aminoacyl residue, or an optionally substituted thioureidyl residue as described in respect of any of subclasses (a) to (f), preferably (a) to (d).

In some embodiments, the invention provides a compound wherein one of $R_1$ and $R_2$ is an optionally substituted glycosyl (preferably as defined in respect of subclass (f)) and the other of $R_1$ and $R_2$ is a substituted alkyl, a succinimidyl derivative, an optionally substituted aminoacyl residue, or an optionally substituted thioureidyl residue, preferably as described in respect of any of subclasses (a) to (e) above. Preferably one of $R_1$ and $R_2$ is an alkyl substituted with an optionally substituted alkylamino (preferably dialkylamino) or carbo- or heterocyclic moiety (preferably a N-linked heterocycloalkyl, optionally substituted with alkyl).

In some embodiments, the invention provides a compound wherein one of one of $R_1$ and $R_2$ is a hydrogen atom; the other of $R_1$ and $R_2$ is a succinimidyl derivative, an optionally substituted benzyl, an optionally substituted thioureidyl residue an optionally substituted aminoacyl residue, preferably as described above in respect of subclasses (a) to (e), preferably (a) to (d).

In some embodiments, the invention provides a compound wherein one of one of $R_1$ and $R_2$ is a hydrogen atom, an unsubstituted alkyl or an alkyl substituted with a carbo- or heterocyclic moiety (preferably a N-linked heterocycloalkyl, optionally substituted with alkyl); the other of $R_1$ and $R_2$ is an alkyl substituted with a carbo- or heterocyclic moiety (preferably a N-linked heterocycloalkyl, optionally substituted with alkyl), preferably as defined in respect of subclass (b).

In any of the compounds of the invention as described herein $R_3$ is a hydroxyl group, alkoxy group or an alkylamino or aminoalkyl derivative. In some embodiments, the invention provides a compound as defined in respect of any of the above embodiments, wherein $R_3$ is hydroxyl, methoxy, or —$NR_{14}$—($C_1$-$C_6$alkyl)-$NR_{15}R_{16}$, wherein $R_{14}$ is a hydrogen atom or methyl, $R_{15}$ and $R_{16}$ are independently chosen from optionally substituted aliphatic, preferably lower alkyl.

In some embodiments, a compound of the invention is not a compound wherein:

(i) $R_3$ is methoxy, one of $R_1$ or $R_2$ is hydrogen, and the other of $R_1$ or $R_2$ is:

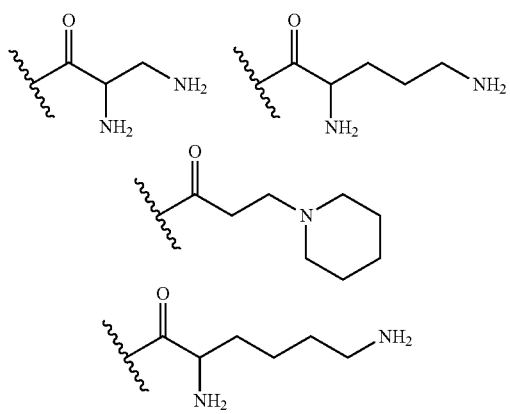

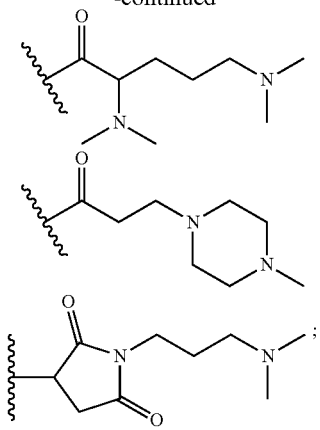

(ii) one of $R_1$ or $R_2$ is hydrogen, the other of $R_1$ or $R_2$ is

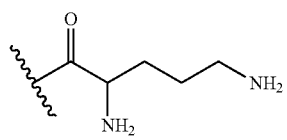

and $R_3$ is

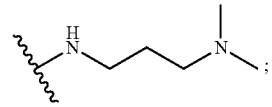 [SMILES: *NCCCN(C)C]

(iii) one of $R_1$ or $R_2$ is hydrogen or unsubstituted alkyl, and the other of $R_1$ or $R_2$ is glycosyl;

(iv) $R_3$ is OH and both of $R_1$ and $R_2$ are 2-aminoethyl, 3-aminopropyl, 3-(Fmoc-amino)propyl, 3-hydroxypropyl, 2,6-diaminohexyl, 3-carboxypropyl, 3-(methyoxycarbonyl) propyl or 2-guanidinoethyl;

(v) both of $R_1$ and $R_2$ are 3-aminopropyl or 3-(Fmoc-amino)propyl and $R_3$ is methoxy, 2-aminoethylamino, 2-(dimethylamino)ethylamino or 3-(4-morpholino)propylamino; or (vi) $R_3$ is hydroxyl, one of $R_1$ or $R_2$ is hydrogen or 2-aminoethyl, and the other of $R_1$ or $R_2$ is 3-aminopropyl or 3(Fmoc-amino)propyl;

or a salt, hydrate or complex thereof.

In some embodiments a compound of the invention is not N-succinyl Amphotericin B, or a salt, hydrate or complex thereof.

In some embodiments, a compound of the invention is not a compound wherein one of $R_1$ or $R_2$ is:

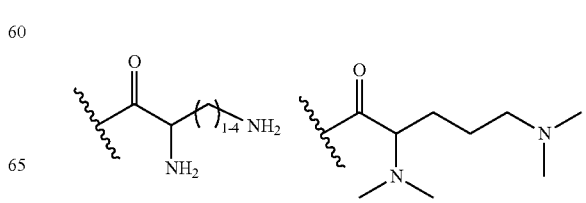

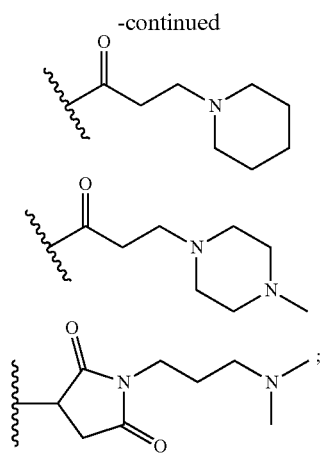

or a salt, hydrate or complex thereof.

In some embodiments, the invention provides a compound of any of the subclasses described above wherein $R_1$ is any of the groups as listed for $R_1$ in Table 1.

In some embodiments, the invention provides a compound of any of the subclasses described above wherein $R_2$ is any of the groups as listed for $R_2$ in Table 1.

In some embodiments, the invention provides a compound of any of the subclasses described above wherein $R_3$ is any of the groups as listed for $R_3$ in Table 1.

In further embodiments, a compound as described herein may be provided in the form of a salt with an inorganic or organic base, preferably as salt with N-methylglucamine.

In further embodiments, a compound as described herein may be provided in the form of a complex with an inorganic or organic complexing compound, preferably as a complex with calcium salt, succinic acid, sodium deoxycholate or a sterol (most preferably with sodium deoxycholate).

In further embodiments, a compound as described herein may be provided in form of salt with an inorganic or organic acid, preferably with aspartic acid.

Any of the salts or complexes as described above may be water soluble.

In another embodiment, the invention provides a compound of Formula 1

$R_2$ is hydrogen atom or substituents such as designed for $R_1$
$R_3$ is hydroxyl group or alkoxyl or alkylamino or an aminoalkyl derivative
and their water soluble salts or complexes, where X is one or more molecules of base or acid or complexing compound.

According to the invention, advantageous N-substituted derivatives, of Formula 1, 1a or 1b, characterized by the presence of bulky substituent at amino group of mycosamine moiety, able to induce steric hindrance effect, were obtained in several exemplary versions, all of which are exemplary embodiments of the invention:

Succinimidyl derivatives of Amphotericin B, exemplary including: N—[N-(2,4,6-trimethylphenyl)succinimidyl]amphotericin B, N—(N-benzylsuccinimidyl)amphotericin B, N—[N-(4-bromophenyl)succinimidyl]amphotericin B, N—[N-(2-tert-butylphenyl)succin imidyl]amphotericin B, N—[N-(4-nitrophenyl)succynimidyl]amphotericin B, N—[N-(2-piperidin-2-ylethyl)succinimidyl]amphotericin B, N-{N-[3-(N,N-dimethylamino)-2,2-dimethylpropyl]succinimidyl}amphotericin B, N—[N-(2-hydroxy-ethyl)succynimidyl]amphotericin B.

In another version of the invention, N-substituted derivatives can be N-thioureidyl derivatives of Amphotericin B, exemplary including: N-[3-(2-piperidin-1-yl)ethylthioureidyl]amphotericin B, N-[(3-phenyl)-thioureidyl]amphotericin B, N-[3-(2-morpholin-1-yl)ethylthioureidyl]amphotericin B, N-{3-[2-(N,N-diethylamino)ethyl]thioureidyl}amphotericin B, N-[3-(pyridin-3-yl)thioureidyl]amfotericin B, N-[3-(2-pirrolidin-1-yl ethyl)thioureidyl]amphotericin B, N-{3-[2-(N,N-dimethylamin)ethyl]thioureidyl}amphotericin B, N-[(3-(pyrydin-4-ylmethyl)thioureidyl]amphotericin B.

In further version according to the invention, N-substituted derivatives can be N,N-dialkyl derivatives of Amphotericin B containing carbocyclic ring, exemplary including: (N,N-dialkylaminobenzyl)amphotericin B or N-alkyl derivatives not containing ring system chosen from the group including: N,N-dimethylamphotericin B, N,N-diethylamphotericin B, N,N-di-n-propylamphotericin B, N,N-di[3-(N-piperidin-1-yl)propyl]amphotericin B, N,N-di[3-(4-ethylpiperazin-1-yl)propyl]amphotericin B, N-(4-N,N-diethylaminobenzyl)amphotericin B, N-[(4-biphenyl)-methyl]amphotericin B, N-(4-tert-butylbenzyl)amphotericin B.

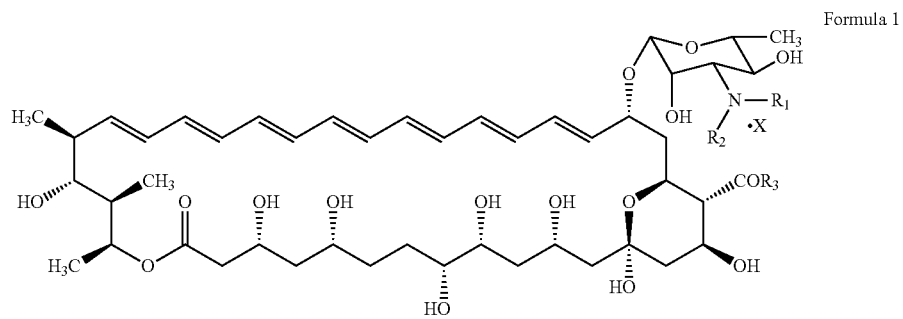

Formula 1 where $R_1$ is hydrogen atom, or alkyl substituent simple or spatially enlarged with 1 to 15 carbon atoms in chain, advantageously as a residue of succinimidyl derivatives or alkyl containing carbo- or heterocyclic ring moieties with ring size 5 to 8 atoms, glycosyl residue, or spatially branched aminoacyl residue or dialkylaminoacyl residue with 1 to 5 carbon atoms in alkyl substituent, thioureidyl residue containing basic nitrogen atom and spatially branched aliphatic or cyclic substituents;

According to another version of the invention, N-substituted derivatives can be N-alkyl derivatives of N-fructosylamphotericin B, exemplary including: N-fructosyl-N-methylamphotericin B, N-fructosyl-N-ethylamphotericin B, N-fructosyl-N-n-propylamphotericin B, N-fructosyl-N—(N,N-dimethyl-3-aminopropyl)amphotericin B, N-fructosyl-N-[3-(piperidin-1-yl)aminopropyl]amphotericin B.

N-substituted derivatives according to the invention can also be N-aminoacyl or N,N-dialkylaminoacyl derivatives of amphotericin B, exemplary including: N-L-phenylalanylamphotericin B, N-L-p-iodophenylalanylamphotericin B, N-D-β-naphtoalanylamphotericin B, N-L-p-nitrophenylalanylamphotericin B, N-methyl-L-(O$^\gamma$-tert-butyl) glutamylamphotericin B, N-D-(O$^\beta$-tert-butyl)asparagyl amphotericin B, N-D-β-(3-(pyridin-3-yl)alanylamphotericin B, N-L-(S-tert-butyl)cystylamphotericin B, N-o-fluorophenylalanylamphotericin B, N-D-(O$^\gamma$-tert-butyl)glutamylamphotericin B, N-D-(O-tert-butyl)-serylamphotericin B, N-D-phenylglycylamphotericin B, N-(L-N,N-diethylphenylalanyl)amphotericin B, N-(L-N,N-dimethylphenyl-alanyl)amphotericin B.

According to the invention N-substituted derivatives of Amphotericin B can be their esters, exemplary including: N-D-β-(pyridin-3-yl)alanylamphotericin B methyl ester, N-[3-(2-piperidin-1-ylethyl)thioureidyl]amphotericin B methyl ester, N-(4-N,N-diethylaminobenzyl)amphotericin B methyl ester.

In another version of the invention N-substituted derivatives can be amide derivatives of Amphotericin B, exemplary including: N-D-β-(pyridin-3-yl)alanylamphotericin B 3-(N,N-dimethylamin)propylamide, N-[3-(2-piperidin-1-yl-ethyl)thioureidyl]amphotericin B 3-(N,N-dimethylamin) propylamide, N-(4-N,N-diethylaminobenzyl) amphotericin B 3-(N,N-dimethylamino)propylamide.

In further version according to the invention N-substituted derivatives can be water soluble salts with inorganic or organic bases, advantageously salts with N-methylglucamine. In another advantageous solution according to the invention, N-substituted derivatives can be water soluble complexes with inorganic or organic complexing compounds.

N-substituted derivatives according to the invention can also be water soluble salts with inorganic or organic acids, advantageously with aspartic acid.

According to the invention the application of above described N-substituted derivatives concerns production of drugs for the treatment of diseases caused by fungal microorganism such as pathogenic yeasts or filamentous fungi or a strain of the genus *Candida*, especially by multidrug resistant (MDR) strains with overexpression of protein transporters MDR1p, as Cdr1p and Cdr2p.

The application of N-substituted derivatives according to the invention concerns also the production of specimens for the control of fungal infections in veterinary, plant protection as well as for protection of buildings from fungal invasion.

The subject of the invention is evidenced below in the examples. In advantageous examples according to the invention, the compounds of structure presented in figure 1, characterized by the presence of bulky moieties, linked to amino group of mycosamine residue which can induce steric hindrance effect, were exemplary obtained in a number of versions presented below.

N-succinimidyl derivatives of the specification from A1 to A8, exemplary include: N—[N-(2,4,6-trimethylphenyl)succinimidyl]amphotericin B (A1), N—(N-benzylsuccinimidyl)amphotericin B (A2), N—[N-(4-bromophenyl)succinimidyl]amphotericin B (A3), N—[N-(2-tert-butylophenyl) succinimidyl]amphotericin B (A4), N—[N-(4-nitrophenyl) succinimidyl]amphotericin B (A5), N—[N-(2-piperidin-1-ylethyl)succinimidyl]amphotericin B (A6), N-{N-[3-(N,N-dimethylamino)-2,2-dimethylpropyl]succinimidyl}amphotericin B (A7), N—[N-(2-hydroxyethyl)succinimidyl]amphotericin B (A8);

N,N-dialkyl derivatives are from A9 to A13 and exemplary including: N,N-dimethylamphotericin B (A9), N,N-diethylamphotericin B (A10), N,N-di-n-propylamphotericin B (A11), N,N-di[3-(N-piperidin-1-yl)propyl]amphotericin B (A12), N,N-di[3-(4-ethylpiperazin-1-yl)propyl]amphotericin B (A13);

N-alkyl derivatives of N-fructosylamphotericin B are from A14 to A18 and exemplary including: N-fructosyl-N-methylamphotericin B (A14), N-ethyl-N-fructosylamphotericin B (A15), N-fructosyl-N-n-propylamphotericin B (A16), N-fructosyl-N—(N,N-dimethyl-3-aminopropyl)amphotericin B (A17), N-fructosyl-N-[3-(piperidin-1-yl) aminopropyl]amphotericin B (A18);

N-benzyl derivatives are from A19 to A21 and exemplary including: N-(4-N,N-diethylaminobenzyl)amphotericin B (A19), N-[(4-biphenyl)methyl]amphotericin B (A20), N-(4-tert-butylbenzyl)amphotericin B (A21);

N-thioureidyl derivatives are from A22 to A29 and exemplary including: N-{[3-(2-piperidin-1-yl)ethyl] thioureidyl}amphotericin B (A22), N-[(3-phenyl)-thioureidyl]amphotericin B (A23), N-{[3-(2-morpholin-1-yl)ethyl] thioureidyl}amphotericin B (A24), N-{3-[2-(N,N-diethylamino)ethyl]thioureidyl}amphotericin B (A25), N-[3-(pyridin-3-yl)thioureidyl]amphotericin B (A26), N-{[3-(2-pyrrolidin-1-yl)ethyl]thioureidyl}amphotericin B (A27), N-{3-[2-(N,N-dimethylamino)ethyl] thioureidyl}amphotericin B (A28), N-{[3-(pyridin-4-yl) methyl]thioureidyl}amphotericin B (A29);

N-aminoacyl derivatives from A30 to A41 and exemplary including: N-L-phenylalanylamphotericin B (A30), N-L-p-iodophenylalanylamphotericin B (A31), N-D-β-naphtylalanylamphotericin B (A32), N-L-p-nitrophenylalanylamphotericin B (A33), N-methyl-L-(O$^\gamma$-tert-butyl) glutamylamphotericin B (A34), N-D-(O$^\beta$-tert-butyl) asparagylamphotericin B (A35), N-D-β-(pyridin-3-yl) alanylamphotericin B (A36), N-L-(S-tert-butyl) cystylamphotericin B (A37), N-o-fluorophenylalanylamphotericin B (A38), N-D-(O$^\gamma$-tert-butyl)glutamylamphotericin B (A39), N-D-(O-tert-butyl) serylamphotericin B (A40), N-D-phenylglycylamphotericin B (A41);

N,N-dialkyloaminoacyl derivatives of Amphotericin B from A42 to A43 and exemplary including: N-(L-N,N-diethylphenylalanyl)amphotericin B (A42), N-(L-N,N-dimethylphenylalanyl)amphotericin B (A43);

Esters of N-substituted derivatives of Amphotericin B from A44 to A46 and exemplary including: N-D-β-(pyridin-3-yl)alanylamphotericin B methyl ester (A44), N-{[3-(2-piperidin-1-yl)ethyl]thioureidyl}amphotericin B methyl ester (A45), N-(4-N,N-diethylaminobenzyl)amphotericin B methyl ester (A46).

Amides of N-substituted derivatives of Amphotericin B from A47 to A49 and exemplary including: N-D-β-(pyridin-3-yl)alanylamphotericin B 3-(N,N-dimethylamino) propylamide (A47), N-{[3-(2-piperidin-1-yl)ethyl] thioureidyl}amphotericin B 3(N,N-dimethylamino) propylamide (A48), N-(4-N,N-diethylaminobenzyl) amphotericin B 3-(N,N-dimethylamino)propylamide (A49). Structure of Amphotericin B derivatives, according to the invention, are presented below in Table 1. Amphotericin B structure is provided for reference purposes.

TABLE 1
Structure of Amphotericin B derivatives.
| Lp | R1 | R2 | R3 | Symbol |
|---|---|---|---|---|
|  | —H | —H | —H | AmB |
|  |  | N-succinimidyl derivatives |  |  |
| 1. | 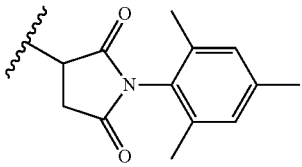 [SMILES: *C1CC(=O)N(c2c(C)cc(C)cc2C)C1=O] | —H | —OH | A1 |
| 2. | 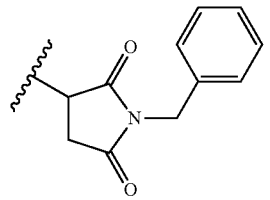 [SMILES: *C1CC(=O)N(Cc2ccccc2)C1=O] | —H | —OH | A2 |
| 3. | 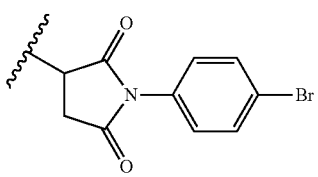 [SMILES: *C1CC(=O)N(c2ccc(Br)cc2)C1=O] | —H | —OH | A3 |
| 4. | 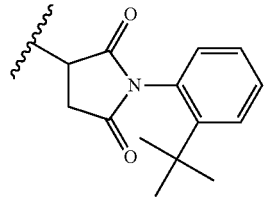 [SMILES: *C1CC(=O)N(c2ccccc2C(C)(C)C)C1=O] | —H | —OH | A4 |
| 5. | 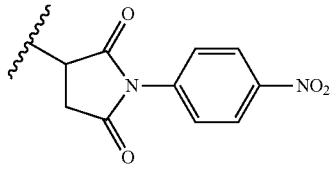 [SMILES: *C1CC(=O)N(c2ccc([N+](=O)[O-])cc2)C1=O] | —H | —OH | A5 |
| 6. | 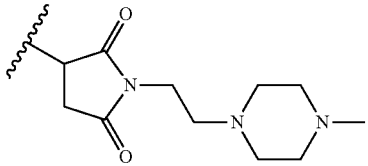 [SMILES: *C1CC(=O)N(CCN2CCN(C)CC2)C1=O] | —H | —OH | A6 |
| 7. | 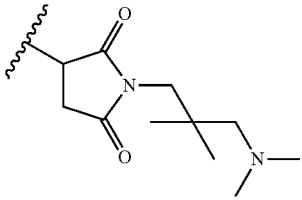 [SMILES: *C1CC(=O)N(CC(C)(C)CN(C)C)C1=O] | —H | —OH | A7 |

TABLE 1-continued
Structure of Amphotericin B derivatives.
| Lp | R1 | R2 | R3 | Symbol |
|---|---|---|---|---|
| 8. | 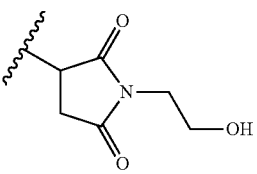 [SMILES: *C1CC(=O)N(CCO)C1=O] | —H | —OH | A8 |
N,N-dialkyl derivatives
| 9. | —CH$_3$ | —CH$_3$ | —OH | A9 |
| 10. | —CH$_2$CH$_3$ | —CH$_2$CH$_3$ | —OH | A10 |
| 11. | —CH$_2$CH$_2$CH$_3$ | —CH$_2$CH$_2$CH$_3$ | —OH | A11 |
| 12. | 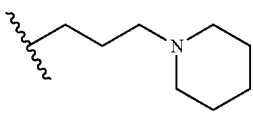 [SMILES: *CCCN1CCCCC1] | 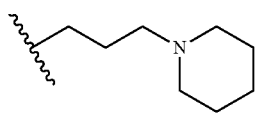 [SMILES: *CCCN1CCCCC1] | —OH | A12 |
| 13. | 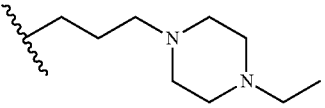 [SMILES: *CCCN1CCN(CC)CC1] | 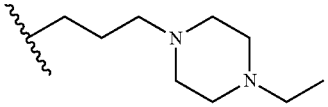 [SMILES: *CCCN1CCN(CC)CC1] | —OH | A13 |
N-alkyl-N-fructosyl derivatives
| 14. | 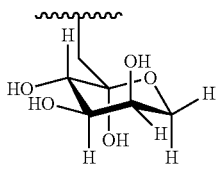 | —CH$_3$ | —OH | A14 |
| 15. | 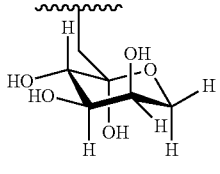 | —CH$_2$CH$_3$ | —OH | A15 |
| 16. | 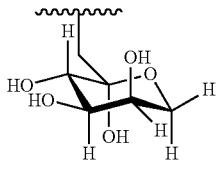 | —CH$_2$CH$_2$CH$_3$ | —OH | A16 |
| 17. | 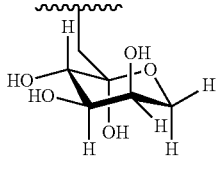 | 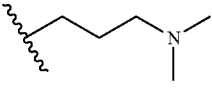 [SMILES: *CCCN(C)C] | —OH | A17 |

TABLE 1-continued

Structure of Amphotericin B derivatives.

| Lp | R1 | R2 | R3 | Symbol |
|---|---|---|---|---|
| 18. | [sugar ring with OH groups] | [chain with piperidine] | —OH | A18 |
| N-benzyl derivatives | | | | |
| 19. | [benzyl with N(Et)₂] | —H | —OH | A19 |
| 20. | [biphenylmethyl] | —H | —OH | A20 |
| 21. | [4-tert-butylbenzyl] | —H | —OH | A21 |
| Thioureidyl derivatives | | | | |
| 22. | [C(=S)NH-CH₂CH₂-piperidine] | —H | —OH | A22 |
| 23. | [C(=S)NH-phenyl] | —H | —OH | A23 |
| 24. | [C(=S)NH-CH₂CH₂-morpholine] | —H | —OH | A24 |
| 25. | [C(=S)NH-CH₂CH₂-N(Et)₂] | —H | —OH | A25 |
| 26. | [C(=S)NH-3-pyridyl] | —H | —OH | A26 |

TABLE 1-continued
Structure of Amphotericin B derivatives.
| Lp | R1 | R2 | R3 | Symbol |
|---|---|---|---|---|
| 27. | 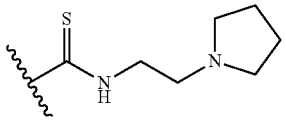 [SMILES: *C(=S)NCCN1CCCC1] | —H | —OH | A27 |
| 28. | 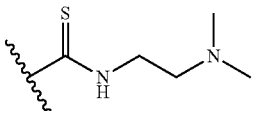 [SMILES: *C(=S)NCCN(C)C] | —H | —OH | A28 |
| 29 | 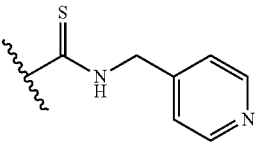 [SMILES: *C(=S)NCc1ccncc1] | —H | —OH | A29 |
| N-aminoacyl derivatives | | | | |
| 30. | 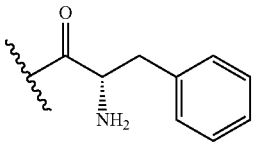 [SMILES: *C(=O)[C@@H](N)Cc1ccccc1] | —H | —OH | A30 |
| 31. | 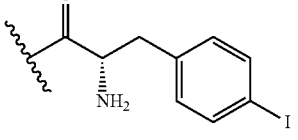 | —H | —OH | A31 |
| 32. | 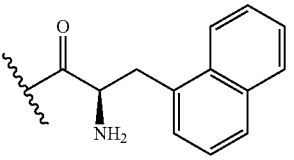 [SMILES: *C(=O)[C@H](N)Cc1cccc2ccccc12] | —H | —OH | A32 |
| 33. | 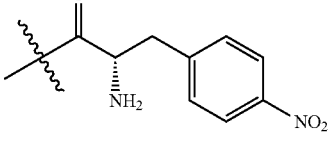 | —H | —OH | A33 |
| 34. | 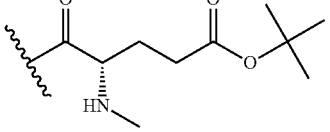 | —H | —OH | A34 |
| 35. | 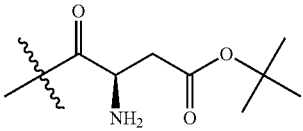 [SMILES: *C(=O)[C@H](N)CC(=O)OC(C)(C)C] | —H | —OH | A35 |

TABLE 1-continued

Structure of Amphotericin B derivatives.

| Lp | R1 | R2 | R3 | Symbol |
|---|---|---|---|---|
| 36. | (C(=O)-CH(NH2)-CH2-(3-pyridyl)) | —H | —OH | A36 |
| 37. | (C(=O)-CH(NH2)-CH2-S-tBu) | —H | —OH | A37 |
| 38. | (C(=O)-CH(NH2)-CH2-(2-fluorophenyl)) | —H | —OH | A38 |
| 39. | (C(=O)-CH(NH2)-CH2-CH2-C(=O)-O-tBu) | —H | —OH | A39 |
| 40. | (C(=O)-CH(NH2)-CH2-O-tBu) | —H | —OH | A40 |
| 41. | (C(=O)-CH(NH2)-Ph) | —H | —OH | A41 |

N,N-dialkylaminoacyl derivatives

| 42. | (C(=O)-CH(CH(Et)2)-CH2-Ph) | —H | —OH | A42 |
| 43. | (C(=O)-CH(N(CH3)2)-CH2-Ph) | —H | —OH | A43 |

Esters and amides of Amphotericin B derivatives

| 44. | (C(=O)-CH(NH2)-CH2-(3-pyridyl)) | —H | —OCH$_3$ | A44 |

TABLE 1-continued

Structure of Amphotericin B derivatives.

| Lp  | R1 | R2 | R3 | Symbol |
|---|---|---|---|---|
| 45. | [structure: thioamide with N-ethyl-piperidine] | —H | —OCH$_3$ | A45 |
| 46. | [structure: benzyl with para-N,N-diethylamino] | —H | —OCH$_3$ | A46 |
| 47. | [structure: α-amino ketone with 3-pyridylmethyl] | —H | —NHCH$_2$CH$_2$CH$_2$N(CH$_3$)$_2$ | A47 |
| 48. | [structure: thioamide with N-ethyl-piperidine] | —H | —NHCH$_2$CH$_2$CH$_2$N(CH$_3$)$_2$ | A48 |
| 49. | [structure: benzyl with para-N,N-diethylamino] | —H | —NHCH$_2$CH$_2$CH$_2$N(CH$_3$)$_2$ | A49 |

The subject of the invention concerns also application of the compounds being sterically hindered derivatives of antifungal antibiotic Amphotericin B of Formula 1, 1a or 1b, where $R_1$ is hydrogen atom or alkyl substituent simple or bulky one, advantageously as a residue of succinimidyl derivative or alkyl containing cyclic moieties carbo- or heterocyclic or glycosyl residue or bulky thioureidyl residue (preferably containing basic nitrogen atom and bulky aliphatic or cyclic substituents), $R_2$ is hydrogen atom or substituents such as defined for $R_1$, while $R_3$ is hydroxyl group or alkoxyl or alkylamino or aminoalkyl derivative also their salts and complexes being water soluble forms, where X is one or more molecules of base or acid or complexing compound, for the combat of fungi, preferably multidrug resistant ones directly or as active components of various formulation of antifungal drugs.

In a second aspect, the invention provides a pharmaceutical composition comprising a compound according to the invention as defined herein. As referenced throughout, a compound according to the invention includes salts, hydrates and complexes thereof.

In a third aspect, the invention provides a compound as defined herein, for use in the treatment of fungal infection. The compound may also be for use in the treatment of diseases caused by fungal infection. Treatment may be in humans or in veterinary medicine.

In a fourth aspect, the invention provides use of a compound in the manufacture of a medicament for the treatment of fungal infection, diseases caused by fungal infection, including treatment in humans or in veterinary medicine.

In a fifth aspect, the invention provides a method of treating diseases caused by fungal infection in a patient comprising administering the patient a therapeutically effective amount of a compound of the invention as defined herein, wherein the patient is a human or animal.

In a sixth aspect, the invention provides the use of a compound of the invention as defined herein for treating a fungal infection in a plant.

In a seventh aspect, the invention provides a plant protection product comprising a compound of the invention as defined herein.

In an eighth aspect, the invention provides a method of treating a fungal infection in a building comprising administering to the building a compound of the invention as defined herein. The compound of the invention may be administered to the building in the form of a solution (preferably an aqueous solution). In some embodiments, the solution may be prepared, for example, by dissolving the compound of the invention (preferably in the form of a powder or granules) in a solvent (preferably water or a water-miscible solvent). In some embodiments, the method of treating a fungal infection in a building comprises applying the solution to the infected area by spraying or brushing.

In a ninth aspect, the invention provides an antifungal building treatment product comprising a compound of the invention as defined herein. The product may be in the form of powder or granules of the compound of the invention, or a solution containing the compound of the invention (preferably an aqueous solution).

Embodiments described herein in relation to the first aspect of the invention (i.e. a compound of the invention) apply mutatis mutandis to the second to ninth aspects of the invention.

In some embodiments, treatment as referred to herein relates to treatment of fungal infections caused by pathogenic fungi from the group of yeasts and filamentous fungi or a strain of the genus *Candida*, optionally wherein the yeasts or fungi have multidrug resistance (MDR), optionally with overexpression of protein transporters MDR1p as Cdr1p and Cdr2p.

Compounds of the invention, when used for preventing or treating a disease, may be administered in an "effective amount". By an "effective amount" it is meant a "therapeutically effective amount", namely an amount of compound sufficient, upon single dose or multiple dose administration, to cause a detectable decrease in disease severity, to prevent advancement of a disease or alleviate disease symptoms beyond that expected in the absence of treatment.

Compounds of the invention are useful for reducing the severity of symptoms of any of the above disorders to be treated. Compounds of the invention are also useful for administration to patients susceptible to, at risk of or suffering from any of the above disorders. Compounds useful for prevention of the above disorders are not required to absolutely prevent occurrence of the disorder in all cases, but may prevent or delay onset of the disorder when administered to a patient susceptible to or at risk of the disorder.

The compounds of the invention may be provided as the free compound or as a suitable salt or hydrate thereof. Salts should be those that are pharmaceutically acceptable and salts and hydrates can be prepared by conventional methods, such as contacting a compound of the invention with an acid or base whose counterpart ion does not interfere with the intended use of the compound. Examples of pharmaceutically acceptable salts include hydrohalogenates, inorganic acid salts, organic carboxylic acid salts, organic sulfonic acid salts, amino acid salt, quaternary ammonium salts, alkaline metal salts, alkaline earth metal salts and the like.

The compounds of the invention can be provided as a pharmaceutical composition. The pharmaceutical composition may additionally comprise a pharmaceutically acceptable excipient for example a pharmaceutically acceptable carrier and/or a pharmaceutically acceptable diluent. Suitable carriers and/or diluents are well known in the art and include pharmaceutical grade starch, mannitol, lactose, magnesium stearate, sodium saccharin, talcum, cellulose, glucose, sucrose (or other sugar), magnesium carbonate, gelatin oil, alcohol, detergents, emulsifiers or water (preferably sterile).

A pharmaceutical composition may be provided in unit dosage form, will generally be provided in a sealed container and may be provided as part of a kit. Such a kit would normally (although not necessarily) include instructions for use. It may include a plurality of said unit dosage forms.

A pharmaceutical composition may be adapted for administration by any appropriate route, for example by the oral (including buccal or sublingual), rectal or topical (including buccal, sublingual or transdermal) route. Such compositions may be prepared by any method known in the art of pharmacy, for example by admixing the active ingredient with a carrier(s) or excipient(s) under sterile conditions.

Pharmaceutical compositions adapted for oral administration may be presented as discrete units such as capsules or tablets; as powders or granules; as solutions, syrups or suspensions (in aqueous or non-aqueous liquids; or as edible foams or whips; or as emulsions). Suitable excipients for tablets or hard gelatine capsules include lactose, maize starch or derivatives thereof, stearic acid or salts thereof. Suitable excipients for use with soft gelatine capsules include for example vegetable oils, waxes, fats, semi-solid, or liquid polyols etc. For the preparation of solutions and syrups, excipients which may be used include for example water, polyols and sugars. For the preparation of suspensions oils (e.g. vegetable oils) may be used to provide oil-in-water or water in oil suspensions.

Pharmaceutical compositions adapted for topical administration may be formulated as ointments, creams, suspensions, lotions, powders, solutions, pastes, gels, sprays, aerosols or oils. For infections of the eye or other external tissues, for example mouth and skin, the compositions are preferably applied as a topical ointment or cream. When formulated in an ointment, the active ingredient may be employed with either a paraffinic or a water-miscible ointment base. Alternatively, the active ingredient may be formulated in a cream with an oil-in-water cream base or a water-in-oil base. Pharmaceutical compositions adapted for topical administration to the eye include eye drops wherein the active ingredient is dissolved or suspended in a suitable carrier, especially an aqueous solvent. Pharmaceutical compositions adapted for topical administration in the mouth include lozenges, pastilles and mouth washes. Pharmaceutical compositions adapted for rectal administration may be presented as suppositories or enemas.

Pharmaceutical compositions adapted for nasal administration wherein the carrier is a solid include a coarse powder having a particle size for example in the range 20 to 500 microns which is administered in the manner in which snuff is taken, i.e. by rapid inhalation through the nasal passage from a container of the powder held close up to the nose. Suitable compositions wherein the carrier is a liquid, for administration as a nasal spray or as nasal drops, include aqueous or oil solutions of the active ingredient.

Pharmaceutical compositions adapted for administration by inhalation include fine particle dusts or mists which may be generated by means of various types of metered dose pressurised aerosols, nebulizers or insufflators. Pharmaceutical compositions adapted for vaginal administration may be presented as pessaries, tampons, creams, gels, pastes, foams or spray formulations.

Pharmaceutical compositions adapted for parenteral administration include aqueous and non-aqueous sterile injection solution which may contain anti-oxidants, buffers, bacteriostats and solutes which render the formulation substantially isotonic with the blood of the intended recipient; and aqueous and non-aqueous sterile suspensions which may include suspending agents and thickening agents. Excipients which may be used for injectable solutions include water, alcohols, polyols, glycerine and vegetable oils, for example. The compositions may be presented in unit-dose or multi-dose containers, for example sealed ampoules and vials, and may be stored in a freeze-dried (lyophilized) condition requiring only the addition of the sterile liquid carried, for example water for injections, immediately prior to use. Extemporaneous injection solutions and suspensions may be prepared from sterile powders, granules and tablets.

The pharmaceutical compositions may contain preserving agents, solubilising agents, stabilising agents, wetting agents, emulsifiers, sweeteners, colourants, odourants, salts, buffers, coating agents or antioxidants. They may also contain an adjuvant and/or therapeutically active agents in addition to the substance of the present invention.

Dosages of the substance of the present invention can vary between wide limits, depending upon a variety of factors including the disease or disorder to be treated, the age, weight and condition of the individual to be treated, the route of administration etc. and a physician will ultimately determine appropriate dosages to be used.

Compositions adapted for the treatment of buildings having a fingal infection can be in the form of a powder or granules to be dissolved in water before use and may be applied to the infected area by spraying or brushing.

Below are described methods for obtaining compounds which are bulky, spatially hindered amphoteric or basic N-alkyl or N-aminoacyl derivatives of antifungal antibiotic of polyene macrolides group, Amphotericin B, of general formula 1, where $R_1$ is hydrogen atom or simple or bulky alkyl substituent, the last one advantageously as residue of succinimide derivative or as branched alkyl or containing carbo- or heterocyclic moieties or glycoyl residue or spatially extended aminoacyl residue or thioureidyl residue containing basic nitrogen atom and bulky aliphatic or cyclic substituents; $R_2$ is hydrogen atom or substituents such as are defined for $R_1$, while $R_3$ is hydroxyl group or alkoxyl or aminoalkyl derivative, also their salts and complexes being their water soluble forms, where X is one or more basic molecules, advantageously N-methyl-D-glucamine one or acid molecule, preferably aspartic acid or complexing agent.

To obtain N-succinimidyl derivatives the reaction of Michael's addition is performed as follows: solution of Amphotericin B in dimethyl formamide, in the presence of triethylamine, is reacted with suitable derivative of maleimide. The obtained product is precipitated with ethyl ether, centrifugated, dried and purified by column chromatography (Silica Gel).

N-aminosuccinimidyl derivatives are obtained in similar manner as N-succinimidyl derivatives but double excess of maleimide derivatives is used. N-thioureidyl derivatives are obtained in the reaction of Amphotericin B, in dimethyl formamide solution, and in the presence of triethylamine, with proper derivatives of isothiocynate. The obtained product is purified by column chromatography (Silica Gel).

N-benzyl derivatives are obtained in the reaction of reductive alkylation in solution of Amphotericin B in dimethyl formamide and methanol, with benzaldehyde or its derivatives, using sodium cyanoborohydride as reducing agent and catalytic amount of acetic acid. The reaction mixture is neutralized with solution of methylamine in tetrahydrofuran, then the final product is precipitated with ethyl ether and purified by column chromatography (Silica Gel).

N-alkyl derivatives of Amphotericin B are obtained in the reaction of reductive alkylation of Amphotericin B, in solution of dimethyl formamide, with aliphatic aldehyde using sodium cyanoborohydride as reducing agent and catalytic amount of acetic acid. The reaction mixture is neutralized with solution of methylamine in tetrahydrofuran, the reaction product is precipitated with ethyl ether and then purified by column chromatography (Silica Gel).

Obtaining of N-alkyl derivatives of N-fructosylamphotericin B is based on method of reductive alkylation of N-fructosylamphotericin B, in solution of dimethyl formamide, with suitable aliphatic aldehyde using sodium cyanoborohydride as reducing agent and catalytic amount of acetic acid. The reaction mixture is neutralized with solution of methylamine in tetrahydrofuran, product is precipitated with ethyl ether and purified by column chromatography (Silica Gel).

N-aminoacyl and N—(N'-alkylamino)acyl derivatives of Amphotericin B are obtained in the reaction of N-acylation of antibiotic by appropriate N-protected aminoacids. First, the reaction of N-(fluorenylmetoxycarbonyl)-aminoacid with N-hydroxysuccinimide in the presence of N,N-'dicyclohexylcarbodiimide is performed in solution of dimethyl formamide. Precipitated N,N'-dicyclohexylurea is removed, then to the rection mixture Amphotericin B and triethylamine are added. Progress of the reaction is monitored by thin layer chromatography. The final product is precipitated with ethyl ether and next purified by column chromatography (Silica Gel).

Synthesis of N—(N,N-dialkylamino)aminoacyl derivatives of Amphotericin B is performed by activation of aminoacid by N-hydroxysuccinimide and N,N-dicyclohexylcarbodiimide in dimethyl formamide solution. Precipitated solid of N,N-dicyclohexylurea is removed, and to the reaction mixture amphotericin B is added. Crude product of the reaction is precipitated with excess of ethyl ether and purified by column chromatography (Silica Gel).

Synthesis of methyl esters of N-substituted Amphotericin B derivatives is performed in the reaction of the antibiotic, in dimethyl formamide solution, with diazomethane which is added to the reaction mixture in ethyl ether solution. Then, excess of diazomethane is removed with acetic acid, the formed product is precipitated by excess of ethyl ether and purified by column chromatography (Silica Gel).

Synthesis of amides of N-substituted Amphotericin B derivatives, for example N-fructosyl-N-propylamphotericin B 3-(N,N-dimethylamino)propyl amide, is performed in the reaction of N-substituted antibiotic derivative, in dimethyl formamide solution, with respective amine in the presence of diphenyl azidephosphate and triethylamine. Product of the reaction is precipitated by excess of ethyl ether and purified by column chromatography (Silica Gel).

Obtaining of salts of amphoteric Amphotericin B derivatives, advantageously with N-methyl-D-glucamine, consist of addition to aqueous suspension of Amphotericin B derivatives of a small excess of N-methyl-D-glucamine diluted in water and precipitation of product by excess of acetone.

Water-soluble complex of amphoteric Amphotericin B derivatives is obtained according to conventional methods.

Water-soluble salts of basic Amphotericin B derivatives, advantageously with aspartic acid, are synthesized by adding to aqueous suspension of antibiotic a slight molar excess of L-aspartic acid, then obtained salt is precipitated by excess of acetone. The method for obtaining sterically hindered Amphotericin B derivatives, according to the invention, univocally leads to obtain the desired product. All obtained compounds have been characterized with respect to their chemical structure and biological properties. Identification of the compounds includes their spectroscopic data as $\lambda_{max}$ determination, extinction value of $E_{1cm}^{1\%}$, molecular weight determined by mass spectrometry MS-ESI, thin layer chromatography with indicated of $R_F$ value. The biological properties of the compounds, according to the invention, were determined using the obligatory standards. There was determined activities of the compounds in vitro against a number of fungal strains, primarily of the genus *Candida* and filament fungi, activity towards multidrug resistance fungal strains with overexpression of protein transporters of both ABC and MFS type. Also hemotoxicity of the compounds was determined by measurement of their hemolytic activity for human erythrocytes as well as their cytotoxicity determined in tissue culture for several mammalian cell lines. The obtained results show that, depending on the kind of steric hindering moieties introduced to Amphotericin B molecule, the compounds exhibit reduced to different extent, in relation to the native antibiotic, hemotoxic activity and are characterized by low cytotoxicity, good antifungal activity and are also active against multidrug resistant strains (MDR).

Compounds according to the invention which are so far unknown sterically hindered derivatives of Amphotericin B, is that they fulfill the basic requirements for antifungal chemotherapeutics. They are characterized by very low hemotoxicity, exhibit low toxicity for mammalian somatic cells, are active against multidrug resistant fungal strains (MDR). Moreover, they form with acids or bases water-soluble salts and also soluble complexes with complexing compounds. The advantage of the compounds according to the invention is also simple and efficient method of their preparation.

The subject of the invention is shown in the below examples, where are presented methods for the preparation and properties of the compounds according to the invention and of their water-soluble salts and complexes.

EXAMPLES

Example 1

Synthesis of N-succinimidyl Derivatives of Amphotericin B 200 mg (0.22 mmol) of Amphotericin B is dissolved in 4 ml of dimethyl formamide (DMF) in 25 ml round-bottomed flask equipped with a magnetic stirrer. The solution is cooled to 0° C. and 0.029 ml (0.21 mmol) of triethylamine (TEA) is slowly added. After 10 minutes 0.25 mmol of the appropriate maleimide is added and the reaction mixture is warmed to room temperature. The reaction progress is monitored by thin layer chromatography (TLC) on Silica Gel (60 F254, Merck) in chloroform: methanol: water (20: 8:1 v/v) solvent system. After then, the reaction mixture is added dropwise to 150 ml of diethyl ether. The resulting, pale yellow precipitate is filtered under reduced pressure on a Millipore funnel. The crude product is twice washed with diethyl ether (2×50 ml) and then dried in a vacuum desiccator. The residue is purified by column chromatography on normal phases, where the solid phase is Silica Gel and solvent system is chloroform: methanol: water (25:8:1 v/v). The fractions with pure product were collected and combined, then evaporated under reduced pressure at temperature not exceeding 35° C. Using in the reaction below indicated maleimides, the following derivatives of Amphotericin B are obtained:

a) In the reaction with N-(2,4,6-trimethylphenyl)maleimide is obtained 30 mg of N—[N-(2,4,6-trimethylphenyl)succinimidyl]amphotericin B (A1)

TLC $R_f$=0.32; UV-vis: $\lambda_{max}$ (MeOH) 406; 382; 363 nm; $E_{1cm}^{1\%}$ (MeOH, $\lambda$=406 nm)=1210 (theoretically for $C_{60}H_{86}N_2O_{19}$ is 1300); MS-ESI found m/z: 1137.4 [M–H$^+$]$^-$; calculated for $C_{60}H_{86}N_2O_{19}$ [M–H]$^-$ 1137.6 b) In the reaction with N-benzylmaleimide is obtained 60 mg of N—(N-benzyl-succinimidyl)amphotericin B (A2)

TLC $R_f$=0.27; UV-vis: $\lambda_{max}$ (MeOH) 406; 382; 363 nm; $E_{1cm}^{1\%}$ (MeOH, $\lambda$=406 nm)=1180 (theoretically for $C_{58}H_{82}N_2O_{19}$ is 1330); MS-ESI found m/z: 1109.3 [M–H$^+$]$^-$; calculated for $C_{58}H_{82}N_2O_{19}$ [M–H]$^-$ 1109.6 c) In the reaction with N-(4-bromophenyl)maleimide is obtained 52 mg of N—[N-(4-bromophenyl)-succinimidyl]amphotericin B (A3)

TLC $R_f$=0.21; UV-vis: $\lambda_{max}$ (MeOH) 406; 382; 363 nm; $E_{1cm}^{1\%}$ (MeOH, $\lambda$=406 nm)=1141 (theoretically for $C_{57}H_{79}BrN_2O_{19}$ is 1260); MS-ESI found m/z: 1207.2 [M+CH$_3$OH]$^-$; calculated for $C_{57}H_{79}BrN_2O_{19}$ [M]$^+$ 1174.5 d) In the reaction with N-(2-tert-butylophenyl)maleimide is obtained 36 mg of N—[N-(2-tert-butylphenyl)succinimidyl]amphotericin B (A4)

TLC $R_f$=0.22; UV-vis: $\lambda_{max}$ (MeOH) 406; 382; 363 nm; $E_{1cm}^{1\%}$ (MeOH, $\lambda$=406 nm)=1236 (theoretically for $C_{61}H_{88}N_2O_{19}$ is 1283); MS-ESI found m/z: 1151.4 [M–H$^+$]$^-$; calculated for $C_1H_{88}N_2O_{19}$ [M]$^{+\cdot}$ 1152.6 e) In the reaction with N-(4-nitrofenylo)maleimid is obtained 40 mg of N—[N-(4-nitro phenyl)succinimidyl]amphotericin B (A5)

TLC $R_f$=0.42; UV-vis: $\lambda_{max}$ (MeOH) 406; 382; 363 nm; $E_{1cm}^{1\%}$ (MeOH, $\lambda$=406 nm)=1261 (theoretically for $C_{57}H_{79}N_3O_{21}$ is 1295); MS-ESI found m/z: 1172.3 [M+CH$_3$OH]$^-$; calculated for $C_{57}H_{79}N_3O_{21}$ [M]$^+$ 1141.5 f) In the reaction with N-(2-hydroxyethyl)maleimid is obtained 56 mg of N—[N-(2-hydroxy-ethyl)succinimidyl]amphotericin B (A8)

TLC $R_f$=0.56; UV-vis: $\lambda_{max}$ (MeOH) 406; 382; 363 nm; $E_{1cm}^{1\%}$ (MeOH, $\lambda$=406 nm)=1350 (theoretically for $C_{53}H_{80}N_2O_{20}$ is 1390); MS-ESI found m/z 1047.5 [M–H$_2$O]$^+$; calculated for $C_{53}H_{80}N_2O_{20}$ [M]$^+$ 1064.5

Example 2

Synthesis of N-aminosuccinimidyl Derivatives of Amphotericin B 200 mg (0.22 mmol) of Amphotericin B is dissolved in 4 ml of dimethyl formamide (DMF) in 25 ml round-bottomed flask equipped with a magnetic stirrer. The solution is cooled to 0° C. and 0.030 ml (0.22 mmol) of triethylamine (TEA) is slowly added. After 10 minutes 0.44 mmol of the appropriate basic maleimide is added and the reaction mixture is warmed to room temperature. The reaction progress is monitored by thin layer chromatography (TLC) on Silica Gel (60 F254, Merck) in chloroform: methanol: water (10: 6:1 v/v) solvent system. After then, the reaction mixture is added dropwise to 150 ml of diethyl ether. The resulting, pale yellow precipitate is filtered under reduced pressure on a Millipore funnel. The crude product is twice washed with diethyl ether (2×50 ml) and then dried in a vacuum desiccator. The residue is purified by column chromatography on normal phases, where the solid phase is Silica Gel and solvent system is chloroform: methanol (gradient from 20% to 80% of methanol) or chloroform: methanol: water (10:6:1 v/v). The fractions with pure product were collected and combined, then evaporated under reduced pressure at temperature not exceeding 35° C. Using in the reaction below indicated basic maleimides, the following derivatives of Amphotericin B are obtained:

g) In the reaction with N-(2-piperidin-1-ylethyl)maleimide is obtained 48 mg of N—[N-(2-piperidin-1-ylethyl)succinimidyl]amphotericin B (A6)

TLC $R_f$=0.18; UV-vis: $\lambda_{max}$ (MeOH) 406; 382; 363 nm; $E_{1cm}^{1\%}$ (MeOH, $\lambda$=406 nm)=1210 (theoretically for $C_{58}H_{90}N_4O_{19}$ is 1290); MS-ESI found m/z: 1147.6 [M+H]$^+$; calculated for $C_{58}H_{90}N_4O_{19}$ [M]$^{+\cdot}$ 1146.6 h) In the reaction with N-[3-(N,N-dimethylamino)-2,2-dimethylpropyl]maleimide is obtained 65 mg of N-{N-[3-(N,N-dimethylamino)-2,2-dimethylpropyl]succinimidyl}-amphotericin B (A7)

TLC $R_f$=0.23; UV-vis: $\lambda_{max}$ (MeOH) 406; 382; 363 nm; $E_{1cm}^{1\%}$ (MeOH, $\lambda$=406 nm)=1210 (theoretically for $C_{58}H_{91}N_3O_{19}$ is 1304); MS-ESI found m/z: 1134.6 [M+H]$^+$; calculated for $C_{58}H_{91}N_3O_{19}$ [M]$^{+\cdot}$ 1133.6

Example 3

Synthesis of N,N-dialkyl Derivatives of Amphotericin B 200 mg (0.22 mmol) of Amphotericin B is dissolved in 3 ml of dimethyl formamide (DMF) in 25 ml round-bottomed flask equipped with a magnetic stirrer. Next, 0.63 mmol of appropriate aliphatic aldehyde is added and solution is stirred at room temperature for 1 hour. After 1 hour 3 ml of anhydrous methanol, 0.63 mmol of sodium cyanoborohydride (NaBH$_3$CN) and catalytic amount of acetic acid (0.015 ml) are added. The reaction progress is monitored by thin layer chromatography (TLC) on Silica Gel (60 F254, Merck) in chloroform:methanol:water (10:6:1 v/v) solvent system. The reaction mixture is cooled at −5° C., and then 0.015 ml of methylamine in tetrahydrofurane is added. The reaction mixture is left for 10 minutes and then added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified on column chromatography on normal phase, where the solid phase is Silica Gel and solvent system is chloroform: methanol: water (10:6:1 v/v) or chloroform:methanol (gradient from 20% to 60% of methanol). The fractions with pure product were collected and combined, then evaporated under reduced pressure at temperatures not exceeding 35° C. The following derivatives of Amphotericin B are obtained:

a) In the reaction with methanal is obtained 40 mg of N,N-dimethylamphotericin B (A9)

TLC $R_f$=0.22; UV-vis: $\lambda_{max}$ (MeOH) 406; 382; 363 nm; $E_{1cm}^{1\%}$ (MeOH, $\lambda$=406 nm)=1290 (theoretically for $C_{49}H_{77}NO_{17}$ is 1554); MS-ESI found m/z: 950.5 [M−H]$^-$; calculated for $C_{49}H_{77}NO_{17}$ [M]$^{+\cdot}$ 951.5 b) In the reaction with ethanal is obtained 37 mg of N,N-diethylamphotericin B (A10)

TLC $R_f$=0.31; UV-vis: $\lambda_{max}$ (MeOH) 406; 382; 363 nm; $E_{1cm}^{1\%}$ (MeOH, $\lambda$=406 nm)=1300 (theoretically for $C_{51}H_{81}NO_{17}$ is 1514); MS-ESI found m/z: 978.5 [M−H$^+$]$^-$; calculated for $C_{51}H_{81}NO_{17}$ [M]$^{+\cdot}$ 979.3 c) In the reaction with propanal is 42 mg of N,N-di-n-propylamphotericin B (A11)

TLC $R_f$=0.27; UV-vis: $\lambda_{max}$ (MeOH) 406; 382; 363 nm; $E_{1cm}^{1\%}$ (MeOH, $\lambda$=406 nm)=1250 (theoretically for $C_{53}H_{87}NO_{17}$ is 1468); MS-ESI found m/z: 1106.6 [M−H$^+$]$^-$; calculated for $C_{53}H_{85}NO_{17}$ [M]$^{+\cdot}$1007.6 d) In the reaction with 3-(N-piperidin-1-ylo)propanal is obtained 20 mg N,N-di[3-(N-piperidin-1-yl)propyl]amphotericin B (A12)

TLC $R_f$=0.31; UV-vis: $\lambda_{max}$ (MeOH) 406; 382; 363 nm; $E_{1cm}^{1\%}$ (MeOH, $\lambda$=406 nm)=1180 (theoretically for $C_{63}H_{103}N_3O_{17}$ is 1258); MS-ESI found m/z: 1175.5 [M+H]$^+$; calculated for $C_{63}H_{103}N_3O_{17}$ [M+H]$^+$ 1175.4 e) In the reaction with 3-(4-ethylpiperazin-1-yl)propanal is obtained 31 mg of N,N-di[3-(4-ethylpiperazin-1-yl)propyl]amphotericin B (A13)

TLC $R_f$=0.26; UV-vis: $\lambda_{max}$ (MeOH) 406; 382; 363 nm; $E_{1cm}^{1\%}$ (MeOH, $\lambda$=406 nm)=1150 (theoretically for $C_{63}H_{105}N_5O_{17}$ is 1226); MS-ESI found m/z: 1205.8 [M+H]$^{+\cdot}$; calculated for $C_{63}H_{105}N_5O_{17}$ [M+H]$^+$ 1205.5

Example 4

Synthesis of N-alkyl Derivatives of N-fructosylamphotericin B 200 mg (0.18 mmol) of N-fructosylamphotericin B is dissolved in 3 ml of dimethyl formamide (DMF) in 25 ml round-bottomed flask equipped with a magnetic stirrer. Next, 0.63 mmol of appropriate aliphatic aldehyde is added and solution is stirred at room temperature for 1 hour. After 1 hour 3 ml of anhydrous methanol, 0.63 mmol of sodium cyanoborohydride and catalytic amount of acetic acid (0.015 ml) are added. The reaction progress is monitored by thin layer chromatography (TLC) on Silica Gel (60 F254, Merck) in chloroform: methanol: water (7:6:1 v/v) or n-butanol:acetic acid:water (4:1:1 v/v) solvent system. The reaction mixture is cooled to −5° C., and then 0.015 ml (2M) of methylamine in tetrahydrofurane is added. The reaction mixture is left for 10 minutes and then is added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase where the solid phase is Silica Gel and solvent system is chloroform: methanol: water (7:6:1 v/v). The fractions with pure product were collected and combined, then evaporated under reduced pressure at temperatures not exceeding 35° C. The following derivatives of N-fructosylamphotericin B are obtained:

a) In the reaction with methanal is obtained 32 mg of N-fructosyl-N-methylamphotericin B (A14)

TLC $R_f$=0.13; UV-vis: $\lambda_{max}$ (MeOH) 406; 382; 363 nm; $E_{1cm}^{1\%}$ (MeOH, $\lambda$=406 nm)=1280 (theoretically for $C_{54}H_{87}NO_{22}$ is 1345); MS-ESI found m/z: 1098.3 [M−H]$^-$; calculated for $C_{54}H_{85}NO_{22}$ [M]$^+$ 1099.6 b) In the reaction with ethanal is obtained 21 mg of N-ethyl-N-fructosylamphotericin B (A15)

TLC $R_f$=0.11; UV-vis: $\lambda_{max}$ (MeOH) 406; 382; 363 nm; $E_{1cm}^{1\%}$ (MeOH, $\lambda$=406 nm)=1230 (theoretically for $C_{55}H_{89}NO_{22}$ is 1328); MS-ESI found m/z: 1112.5 [M−H]$^-$; calculated for $C_{55}H_{87}NO_{22}$ [M]$^+$ 1113.4 c) In the reaction with propanal is obtained 28 mg of N-fructosyl-N-n-propylamphotericin B (A16)

TLC $R_f$=0.14; UV-vis: $\lambda_{max}$ (MeOH) 406; 382; 363 nm; $E_{1cm}^{1\%}$ (MeOH, $\lambda$=406 nm)=1210 (theoretically for $C_{56}H_{91}NO_{22}$ is 1311); MS-ESI found m/z: 1126.4 [M−H]$^-$; calculated for $C_{56}H_{89}NO_{22}$ [M]$^{+\cdot}$ 1127.6 d) In the reaction with N,N-dimethyl-3-aminopropanal is obtained 15 mg of N-fructosyl-N—(N,N-dimethyl-3-aminopropyl)amphotericin B (A17)

TLC $R_f$=0.11; UV-vis: $\lambda_{max}$ (MeOH) 406; 382; 363 nm; $E_{1cm}^{1\%}$ (MeOH, $\lambda$=406 nm)=1120 (theoretically for $C_{58}H_{94}N_2O_{22}$ is 1261); MS-ESI found m/z: 1172.7 [M+H]$^+$; calculated for $C_{58}H_{94}N_2O_{22}$ [M+H]$^+$ 1172.5 e) In the reaction with 3-(piperidin-1-yl)propanal is obtained 28 mg N-fructosyl-N-[3-(piperidin-1-yl)aminopropyl] amphotericin B (A18)

TLC $R_f$=0.15; UV-vis: $\lambda_{max}$ (MeOH) 406; 382; 363 nm; $E_{1cm}^{1\%}$ (MeOH, $\lambda$=406 nm)=1180 (theoretically for $C_{61}H_{98}N_2O_{22}$ is 1221); MS-EI found m/z: 1211.9 [M+H]$^+$; calculated for $C_{61}H_{98}N_2O_{22}$ [M+H]$^+$ 1211.5

Example 5

Synthesis of N-benzyl Derivatives of Amphotericin B 200 mg (0.22 mmol) of Amphotericin B is dissolved in 3 ml of dimethyl formamide (DMF) in 25 ml round-bottomed flask equipped with a magnetic stirrer. Next, 0.3 mmol of aromatic aldehyde is added and stirred at room temperature for 1 hour. After 1 hour 3 ml of anhydrous methanol, 0.3 mmol of sodium cyanoborohydride (NaBH$_3$CN) and catalytic amount (0.015 ml) of acetic acid are added. The reaction progress is monitored by thin layer chromatography (TLC) on Silica Gel (60 F254, Merck) in chloroform: methanol: water (20:6:1 v/v) solvent system. The reaction mixture is cooled to −5° C., and then 0.015 ml of methylamine in tetrahydrofurane is added. The reaction mixture is left for 10 minutes and then added dropwise to 150 ml of diethyl ether. The resulting pale yellow precipitate is filtered under reduced pressure on a Millipore funnel. The crude product is twice washed with diethyl ether (2×50 ml) and then dried in a vacuum dessicator. The residue is purified by column chromatography on normal phase, where the solid phase is Silica Gel and solvent system is chloroform: methanol: water (20:6:1 v/v). The fractions with pure product were collected and combined, then evaporated under reduced pressure at temperatures not exceeding 35° C. The following derivatives of Amphotericin B are obtained:

a) In the reaction with z 4-(N,N-diethylamino)benzaldehyde is obtained 15 mg of N-(4-N,N-diethylaminobenzyl)amphotericin B (A19)

TLC $R_f$=0.75; UV-vis: $\lambda_{max}$ (MeOH) 406; 382; 363 nm; $E_{1cm}^{1\%}$ (MeOH, $\lambda$=406 nm)=1150 (theoretically for $C_{58}H_{88}N_2O_{17}$ is 1363); MS-ESI found m/z: 1083.3 [M−H]$^-$; calculated for $C_{58}H_{88}N_2O_{17}$ [M]$^{+\bullet}$ 1084.6 b) In the reaction with 4-phenylbenzaldehyde is obtained 45 mg of N-[(4-biphenyl)-methyl]amphotericin B (A20)

TLC $R_f$=0.86; UV-vis: $\lambda_{max}$ (MeOH) 406; 382; 363 nm; $E_{1cm}^{1\%}$ (MeOH, $\lambda$=406 nm)=1230 (theoretically for $C_{60}H_{83}NO_{17}$ is 1357); MS-ESI found m/z: 1088.8 [M−H]$^-$; calculated for $C_{60}H_{83}NO_{17}$ [M]$^{+\bullet}$ 1089.6 c) In the reaction with z 4-tert-butylbenzaldehyde is obtained 47 mg of N-(4-tert-butylobenzylo)amphotericin B (A21)

TLC $R_f$=0.87; UV-vis: $\lambda_{max}$ (MeOH) 406; 382; 363 nm; $E_{1cm}^{1\%}$ (MeOH, $\lambda$=406 nm)=1200 (theoretically for $C_{54}H_{81}NO_{17}$ is 1382); MS-ESI found m/z: 1068.5 [M−H]$^-$; calculated for $C_{58}H_{87}NO_{17}$ [M]$^{+\bullet}$ 1069.6

Example 6

Synthesis of N-thioureidyl Derivatives of Amphotericin B 200 mg (0.22 mmol) of Amphotericin B is dissolved in 4 ml of dimethyl formamide (DMF) in 100 ml round-bottomed flask equipped with a magnetic stirrer. The solution is cooled to 0° C. and 0.029 ml (0.21 mmol) of triethylamine (TEA) is slowly added. After 10 minutes 0.25 mmol of the appropriate isothiocyanate is added and the reaction mixture is warmed to room temperature. The reaction progress is monitored by thin layer chromatography (TLC) on Silica Gel (60 F254, Merck) in chloroform: methanol: water (10:6:1 v/v) solvent system. After then the reaction mixture is added dropwise to 150 ml of diethyl ether. The resulting, pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform: methanol (gradient from 20% to 55% of methanol). The fractions with pure product were collected and combined, then evaporated under reduced pressure at temperature not exceeding 35° C. The following derivatives of Amphotericin B are obtained:

a) In the reaction with 2-piperidin-1-yl-ethylisothiocyanate is obtained 35 mg of N-{[3-(2-piperidin-1-yl)ethyl]thioureidyl]amphotericin B (A22)

TLC $R_f$=0.4; UV-vis: $\lambda_{max}$ (MeOH) 406; 382; 363 nm; $E_{1cm}^{1\%}$ (MeOH, $\lambda$=406 nm)=1230 (theoretically for $C_{55}H_{87}N_3O_{17}S$ is 1352); MS-ESI found m/z: 1094.5 [M+H]$^+$; calculated for $C_{55}H_{87}N_3O_{17}S$ [M]$^{+\bullet}$ 1093.6 b) In the reaction with phenylisothiocyanate is obtained 10 mg of N-[(3-phenyl)-thioureidyl]amphotericin B (A23)

TLC $R_f$=0.85; UV-vis: $\lambda_{max}$ (MeOH) 406; 382; 363 nm; $E_{1cm}^{1\%}$ (MeOH, $\lambda$=406 nm)=1320 (theoretically for $C_{54}H_{78}N_2O_{17}S$ is 1397); ESI-MS found m/z: 1057.5 [M−H]$^-$; calculated for $C_{54}H_{78}N_2O_{17}S$ [M]$^{+\bullet}$ 1058.5 c) In the reaction with 2-(1-morpholin-1-yl)ethylisothiocyanate is obtained 23 mg of N-{[3-(2-morpholin-1-yl)ethyl]thioureidyl}amphotericin B (A24)

TLC $R_f$=0.5; UV-vis: $\lambda_{max}$ (MeOH) 406; 382; 363 nm; $E_{1cm}^{1\%}$ (MeOH, $\lambda$=406 nm)=1290 (theoretically for $C_{54}H_{87}N_3O_{18}S$ is 1348); MS-ESI found m/z: 1096.4[M+H]$^+$; calculated for $C_{54}H_{87}N_3O_{18}S$ [M]$^{+\bullet}$ 1095.6 d) In the reaction with N,N-diethyl-2-aminoethylisothiocyanate is obtained 44 mg of N-{3-[2-(N,N-diethylamino)ethyl]thioureidyl}amphotericin B (A25)

TLC $R_f$=0.32; UV-vis: $\lambda_{max}$ (MeOH) 406; 382; 363 nm; $E_{1cm}^{1\%}$ (MeOH, $\lambda$=406 nm)=1240 (theoretically for $C_{55}H_{89}N_3O_{17}S$ is 1350); MS-ESI found m/z: 1096.5 [M+H]$^+$; calculated for $C_{55}H_{89}N_3O_{17}S$ [M]$^{+\bullet}$ 1095.6 e) In the reaction with (pyridin-3-yl)isothiocyanate is 130 mg of N-[3-(pyridn-3-yl)thioureidyl]amphotericin B (A26)

TLC $R_f$=0.83; UV-vis: $\lambda_{max}$ (MeOH) 406; 382; 363 nm; $E_{1cm}^{1\%}$ (MeOH, $\lambda$=406 nm)=1280 (theoretically for $C_{53}H_{77}N_3O_{17}S$ is 1396); MS-ESI found m/z: 1060.5 [M+H]$^+$; calculated for $C_{53}H_{77}N_3O_{17}S$ [M]$^{+\bullet}$ 1059.5 f) In the reaction with 2-(pyrrolidin-1-yl)ethyloisothiocyanate is obtained 25 mg of N-{[3-(2-pyrrolidin-1-yl)ethyl)thioureidyl]amphotericin B (A27)

TLC $R_f$=0.38; UV-vis: $\lambda_{max}$ (MeOH) 406; 382; 363 nm; $E_{1cm}^{1\%}$ (MeOH, $\lambda$=406 nm)=1270 (theoretically for $C_{54}H_{85}N_3O_{17}S$ is 1370); MS-ESI found m/z: 1080.1 [M+H]$^+$; calculated for $C_{54}H_{85}N_3O_{17}S$ [M]$^{+\bullet}$ 1079.6 g) In the reaction with 2-(N,N-dimethylamino)ethylisothiocyanate is obtained 38 mg of N-{3-[2-(N,N-dimethylamino)ethyl]thioureidyl}amphotericin B (A28)

TLC $R_f$=0.33; UV-vis: $\lambda_{max}$ (MeOH) 406; 382; 363 nm; $E_{1cm}^{1\%}$ (MeOH, $\lambda$=406 nm)=1320 (theoretically for $C_{52}H_{83}N_3O_{17}S$ is 1400); MS-ESI found m/z: 1054.4 [M+H]$^+$; calculated for $C_{52}H_{83}N_3O_{17}S$ [M]$^{+\bullet}$ 1053.5 h) In the reaction with (pyridin-4-yl)methylisothiocyanate is obtained 40 mg N-{[3-(pyridin-4-yl)methyl)thioureidyl] amphotericin B (A29)

TLC $R_f$=0.73; UV-vis: $\lambda_{max}$ (MeOH) 406; 382; 363 nm; $E_{1cm}^{1\%}$ (MeOH, $\lambda$=406 nm)=1190 (theoretically for $C_{53}H_{77}N_3O_{17}S$ is 1377); MS-ESI found m/z: 1074.6 [M+H]$^+$; calculated for $C_{54}H_{79}N_3O_{17}S$ [M]$^{+\cdot}$ 1073.5

Example 7

Synthesis of N-aminoacyl and N—(N'-alkylamino)Acyl Derivatives of Amphotericin B 0.26 mmol of N-(9-fluorenylmethoxycarbonyl)aminoacid (Fmoc-aminoacid), 0.26 mmol of N-hydroxysuccinimide (HONSu), 53 mg (0.26 mmol) of dicyclohexylcarbodiimide (DCC) is dissolved in 3 ml of dimethyl formamide (DMF) in 25 ml round-bottomed flask equipped with a magnetic stirrer. The reaction mixture is stirred at 37° C. for 1 hour. The reaction progress is monitored by thin layer chromatography (TLC) on Silica Gel (60 F254, Merck) in ethyl acetate:hexane (7:3 v/v) solvent system. During the reaction, the precipitated N,N-dicyclohexylurea is filtered and washed with 1 ml of DMF. To the filtrate 200 mg (0.22 mmol) of Amphotericin B and 0.04 ml (0.22 mmol) of triethylamine (TEA) are added. Stirring is continued at 37° C. for 3 hours. After the reaction, another portion of 0.04 ml (0.22 mmol) of TEA is added and the reaction mixture is left for 2 hours at room temperature, and then added dropwise to 150 ml of diethyl ether. The resulting, pale yellow precipitate is filtered under reduced pressure on a Millipore funnel. The crude product is washed twice with diethyl ether (2×50 ml) and then dried in a vacuum desiccators. The residue is purified on column chromatography on normal phase, where the solid phase is Silica Gel and solvent system is chloroform: methanol: water (15:8:1 v/v). The fractions with pure product were collected and combined, then evaporated under reduced pressure at temperature not exceeding 35° C. The following derivatives of Amphotericin B are obtained in the reaction with the corresponding protected amino acids:

a) In the reaction with N-Fmoc-L-phenylalanine is obtained 56 mg of N-L-phenylalanylamphotericin B (A30)

TLC R$_f$=0.41; UV-vis: $\lambda_{max}$ (MeOH) 406; 382; 363 nm; E$_{1cm}^{1\%}$ (MeOH, $\lambda$=406 nm)=1280 (theoretically for $C_{56}H_{84}N_2O_{18}$ is 1380); MS-ESI found m/z: 1073.9 [M+H]$^+$; 1096 [M+Na]$^+$; calculated for $C_{56}H_{84}N_2O_{18}$ [M]$^{+\cdot}$ 1072.6 b) In the reaction with N-Fmoc-L-p-iodophenylalanine is obtained 35 mg of N-L-p-iodophenylalanylamphotericin B (A31)

TLC R$_f$=0.53; UV-vis: $\lambda_{max}$ (MeOH) 406; 382; 363 nm; E$_{1cm}^{1\%}$ (MeOH, $\lambda$=406 nm)=1130 (theoretically for $C_{56}H_{84}N_2O_{18}$ is 1233); MS-ESI found m/z: 1199.9 [M+H]$^+$; calculated for $C_{56}H_{83}IN_2O_{18}$ [M]$^{+\cdot}$ 1198.5 c) In the reaction with N-Fmoc-D-β-naphtylalanine is obtained 30 mg N-D-β-naphtylalanylamphotericin B (A32)

TLC R$_f$=0.40; UV-vis: $\lambda_{max}$ (MeOH) 406; 382; 363 nm; E$_{1cm}^{1\%}$ (MeOH, $\lambda$=406 nm)=1150 (theoretically for $C_{60}H_{86}N_2O_{18}$ is 1317); MS-ESI found m/z: 1124.9 [M+H]$^+$; 1189.9 [M+2MeOH]$^+$; calculated $C_{60}H_{86}N_2O_{18}$ [M]$^{+\cdot}$ 1122.6 d) In the reaction with N-Fmoc-L-p-nitrophenylalanine is obtained 23 mg of N-L-p-nitrophenylalanylamphotericin B (A33)

TLC R$_f$=0.41; UV-vis: $\lambda_{max}$ (MeOH) 406; 382; 363 nm; E$_{1cm}^{1\%}$ (MeOH, $\lambda$=406 nm)=1240 (theoretically for $C_{56}H_{83}N_3O_{20}$ is 1323); MS-ESI found m/z: 1119.9 [M+H]$^+$; calculated for $C_{56}H_{83}N_3O_{20}$ [M]$^{+\cdot}$ 1117.6 e) In the reaction with N-Fmoc-N-methyl-L-(O$^\gamma$-tert-butyl) glutamic acid is obtained 20 mg of N-methyl-L-(O$^\gamma$-tert-butyl)glutamylamphotericin B (A34)

TLC R$_f$=0.24; UV-vis: $\lambda_{max}$ (MeOH) 406; 382; 363 nm; E$_{1cm}^{1\%}$ (MeOH, $\lambda$=406 nm)=1230 (theoretically for $C_{57}H_{92}N_2O_{20}$ is 1315); MS-ESI found m/z 1126: [M+H]$^+$; 1158 [M+MeOH]$^+$; calculated for $C_{57}H_{92}N_2O_{20}$ [M]$^{+\cdot}$ 1124.6 f) In the reaction with N-Fmoc-D-(O$^\beta$-tert-butyl)asparagine is obtained 30 mg of N-D-(O$^\beta$-tert-butyl)asparagylamphotericin B (A35)

TLC R$_f$=0.35; UV-vis: $\lambda_{max}$ (MeOH) 406; 382; 363 nm; E$_{1cm}^{1\%}$ (MeOH, $\lambda$=406 nm)=1270 (theoretically for $C_{55}H_{88}N_2O_{20}$ is 1348); MS-ESI found m/z: 1098 [M+H]$^+$; 1164 [M+MeOH]$^+$; calculated for $C_{55}H_{88}N_2O_{20}$ [M]$^{+\cdot}$ 1096.6 g) In the reaction with N-Fmoc-D-β-(pyridin-3-yl)alanine is obtained 70 mg of N-D-β-(pyridin-3-yl)alanylamphotericin B (A36)

TLC R$_f$=0.37; UV-vis: $\lambda_{max}$ (MeOH) 406; 382; 363 nm; E$_{1cm}^{1\%}$ (MeOH, $\lambda$=406 nm)=1240 (theoretically for $C_{55}H_{81}N_3O_{18}$ is 1380); MS-ESI found m/z: 1070.3 [M-H]$^-$; calculated for $C_{55}H_{81}N_3O_{18}$ [M]$^{+\cdot}$ 1071.6 h) In the reaction with N-Fmoc-L-(S-tert-butyl)cysteine is obtained 80 mg N-L-(S-tert-butyl)cystylamphotericin B (A37)

TLC R$_f$=0.34; UV-vis: $\lambda_{max}$ (MeOH) 406; 382; 363 nm; E$_{1cm}^{1\%}$ (MeOH, $\lambda$=406 nm)=1280 (theoretically for $C_{54}H_{86}N_2O_{18}S$ is 1366); MS-ESI found m/z: 1081.5 [M-H]$^-$; calculated for $C_{54}H_{86}N_2O_{18}S$ [M]$^{+\cdot}$ 1082.5 i) In the reaction with rac-N-Fmoc-o-fluorophenylalanine is obtained 23 mg N-o-fluorophenylalanylamphotericin B (A38)

TLC R$_f$=0.41; UV-vis: $\lambda_{max}$ (MeOH) 406; 382; 363 nm; E$_{1cm}^{1\%}$ (MeOH, $\lambda$=406 nm)=1290 (theoretically for $C_{56}H_{81}FN_2O_{18}$ is 1360); MS-ESI found m/z: 1087.2 [M-H]$^-$; calculated for $C_{56}H_{81}FN_2O_{18}$ [M]$^{+\cdot}$ 1188.5 j) In the reaction with N-Fmoc-D-(O$^\gamma$-tert-butyl)glutamic acid is obtained 56 mg of N-D-(O$^\gamma$-tert-butyl)glutamylamphotericin B (A39)

TLC R$_f$=0.26; UV-vis: $\lambda_{max}$ (MeOH) 406; 382; 363 nm; E$_{1cm}^{1\%}$ (MeOH, $\lambda$=406 nm)=1270 (theoretically for $C_{56}H_{88}N_2O_{20}$ is 1334); MS-ESI found m/z: 1107.4 [M-H]$^-$; calculated for $C_{56}H_{88}N_2O_{20}$ [M]$^{+\cdot}$ 1108.6 k) In the reaction with N-Fmoc-D-(O-tert-butyl)serine is obtained 106 mg N-D-(O-tert-butyl)serylamfotericin B (A40)

TLC R$_f$=0.35; UV-vis: $\lambda_{max}$ (MeOH) 406; 382; 363 nm; E$_{1cm}^{1\%}$ (MeOH, $\lambda$=406 nm)=1310 (theoretically for $C_{54}H_{86}N_2O_{19}$ is 1386); MS-ESI found m/z: 1065.7 [M-H]$^-$; calculated for $C_{54}H_{86}N_2O_{19}$ [M]$^{+\cdot}$ 1066.6 l) In the reaction with N-Fmoc-D-phenylglycyne is obtained 82 mg N-D-phenyloglycylamphotericin B (A41)

TLC R$_f$=0.35; UV-vis: $\lambda_{max}$ (MeOH) 406; 382; 363 nm; E$_{1cm}^{1\%}$ (MeOH, $\lambda$=406 nm)=1280 (theoretically for $C_{55}H_{82}N_2O_{18}$ is 1400); MS-ESI found m/z: 1081.3 [M+Na]$^+$; calculated for $C_{55}H_{80}N_2O_{18}$ [M]$^{+\cdot}$ 1056.5

Example 8

Synthesis of N—(N',N'-dialkyl)Aminoacyl Derivatives of Amphotericin B 0.44 mmol of aminoacid, 0.44 mmol of N-hydroxysuccinimide (HONSu), 0.44 mmol (0.26 mmol) of dicyclohexylcarbodiimid (DCC) is dissolved in 3 ml of dimethyl formamide (DMF) in 25 ml round-bottomed flask equipped with a magnetic stirrer. The reaction mixture is stirred at 37° C. for 1 hour. The reaction progress is monitored by thin layer chromatography (TLC) on Silica Gel (60 F254, Merck) in ethyl acetate:hexane (7:3 v/v) solvent system. During the reaction precipitated N,N'-dicyclohexylurea is filtered and washed with 1 ml DMF. To the filtrate 200 mg (0.22 mmol) of Amphotericin B and 0.04 ml (0.22 mmol) of triethylamine are added. The reaction progress is monitored by thin layer chromatography (TLC) on Silica Gel (60 F254, Merck) in chloroform: methanol: water (10:6:1 v/v) solvent system. Stirring is continued at 37° C. for 6-16 hours. After then the reaction mixture is added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform: methanol: water (10:6:1 v/v). The fractions containing pure product were collected and combined, then evaporated under reduced pressure at temperature not exceeding 35° C. The following derivatives of Amphotericin B are obtained in the reaction with the corresponding amino acids:

a) In the reaction with N,N-diethyl-L-phenylalanine is obtained 48 mg of N-(L-N,N-diethylphenylalanyl)amphotericin B (A42)

TLC $R_f$=0.49; UV-vis: $\lambda_{max}$ (MeOH) 406; 382; 363 nm; $E_{1cm}^{1\%}$ (MeOH, $\lambda$=406 nm)=1210 (theoretically for $C_{60}H_{90}N_2O_{18}$ is 1312); MS-ESI found m/z: 1125.4 [M–H]$^-$; calculated for $C_{60}H_{90}N_2O_{18}$ [M]$^{+\cdot}$ 1126.6 b) In the reaction with N,N-dimethyl-L-phenylalanine is obtained 155 mg of N-(L-N,N-dimethylphenylalanyl)amphotericin B (A43)

TLC $R_f$=0.42; UV-vis: $\lambda_{max}$ (MeOH) 406; 382; 363 nm; $E_{1cm}^{1\%}$ (MeOH, $\lambda$=406 nm)=1210 (theoretically for $C_{58}H_{86}N_2O_{18}$ is 1346); MS-ESI found m/z: 1097.6 [M–H]$^-$; calculated for $C_{58}H_{86}N_2O_{18}$[M]$^{+\cdot}$ 1098.6

Example 9

Synthesis of Methyl Esters of N-substituted Derivatives of Amphotericin B 0.1 mmol of Amphotericin B derivative is dissolved in a mixture of dimethyl formamide/methanol (3 ml/1 ml), next mixture was cooled to 5 C and excess of diazomethane (ether solution) in a molar ratio of 1:2.5 is added. The reaction mixture is left for 2 hour at 0° C. The reaction progress is monitored by thin layer chromatography (TLC) on Silica Gel (60 F254, Merck) in chloroform: methanol: water (10:6:1 v/v) solvent system. After then the excess of diazomethane is decomposed with acetic acid, and the reaction mixture is added dropwise to 150 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform: methanol: water (15:6:1 v/v). The fractions containing product were collected and combined, then evaporated under reduced pressure at temperature not exceeding 35° C. In the case of an ester derivatives of Amphotericin B with the protected amino group, the purified product was dissolved in DMF and treated with equimolar amounts of DBN (1,5-diazabicyclo[4.2.0]non5-en) in order to remove the protected group. The reaction progress is monitored by thin layer chromatography (TLC) on Silica Gel (60 F254, Merck) in chloroform: methanol: water (10:6:1 v/v) solvent system. After the reaction excess of diethyl ether is added, the resulting pale yellow precipitate is filtered under reduced pressure on a Millipore funnel. In manner described above, exemplary is obtained 40 mg of N-D-β-(pyridin-3-yl)alanylamphotericin B methyl ester (A44)

TLC $R_f$=0.57; UV-vis: $\lambda_{max}$ (MeOH) 406; 382; 363 nm; $E_{1cm}^{1\%}$ (MeOH, $\lambda$=406 nm)=1250 (theoretically is $C_{56}H_{83}N_3O_{18}$: is 1362); MS-ESI found m/z: 1084.3 [M–H]$^-$; calculated for $C_{56}H_{83}N_3O_{18}$ [M]$^{+\cdot}$ 1085.6

Example 10

Synthesis of Amides of N-substituted Derivatives of Amphotericin B 0.1 mmol of Amphotericin B derivative is dissolved in 5 ml of dimethyl formamide (DMF) in the round-bottomed flask equipped with a magnetic stirrer. The mixture was cooled to 0° C. and 102 mg (1 mmol) of 3-N, N-dimethylpropyldiamine, 275 (1 mmol) of diphenyl azidephosphate (DPPA), and 14 ml (1 mmol) triethyl amine (TEA) are added. The reaction mixture is left for 24 hours. The reaction progress is monitored by thin layer chromatography (TLC) on Silica Gel (60 F254, Merck) in chloroform: methanol: water (10:6:1 v/v) solvent system. The reaction mixture is added dropwise to 100 ml of diethyl ether. The resulting pale yellow precipitate is filtered under reduced pressure on a Millipore funnel. The crude product is twice washed with diethyl ether (2×50 ml) and then dried in a vacuum desiccator. The residue is purified by column chromatography on normal phase, where the solid phase is Silica Gel and solvent system is chloroform: methanol: water (15:6:1 v/v). The fractions containing product were collected and combined, then evaporated under reduced pressure at temperature not exceeding 35° C. In the case of an amide derivative of Amphotericin B with the protected amino group, the purified product was dissolved in DMF and treated with equimolar amounts of DBN (1,5-diazabicyclo[4.2.0]non5-en) in order to remove the protected group. The reaction progress is monitored by thin layer chromatography (TLC) on Silica Gel (60 F254, Merck) in chloroform: methanol: water (10:6:1 v/v) solvent system. After the reaction excess of diethyl ether is added, the resulting pale yellow precipitate is filtered under reduced pressure on a Millipore funnel. In manner described above, exemplary is obtained 21 mg of N-D-β-(pyridn-3-yl)alanylamphotericin B 3-(N,N-dimethylamino)propylamide (A47)

TLC $R_f$=0.52; UV-vis: $\lambda_{max}$ (MeOH) 406; 382; 363 nm; $E_{1cm}^{1\%}$ (MeOH, $\lambda$=406 nm)=1150 (theoretically for $C_{59}H_{91}N_5O_{17}$ is 1220); MS-ESI found m/z: 1210.3 [M–H]$^-$; calculated for $C_{59}H_{91}N_5O_{17}$ [M]$^{+\cdot}$ 1211.6

Example 11

Preparation of Salts with N-methyl-D-glucamine of Amphoteric Amphotericin B Derivatives 0.1 mmol derivative of Amphotericin B in 2 ml of deionized water is suspended in round-bottomed flask equipped with a magnetic stirrer and then 0.11 mmol of N-methyl-D-glucamine dissolved in 1 ml of water is added. Next, to the solution excess of acetone is added. The resulting pale yellow precipitate is filtered under reduced pressure on a Millipore funnel. The crude product is twice washed with diethyl ether (2×50 ml) and then dried in a vacuum desiccator. In the manner described above exemplary is obtained 89 mg of N-methyl-D-glucamine salt of N-D-β-(pyridin-3-yl)alanylamphotericin B (A50)

UV-vis: $\lambda_{max}$ (MeOH) 406; 382; 363 nm; $E_{1cm}^{1\%}$ (MeOH, $\lambda$=406 nm)=1190 (theoretically for $C_{62}H_{100}N_4O_{23}$ is 1267.9).

Example 12

Preparation of Salts with L-aspartic Acids of Basic or Amphoteric Derivatives of Amphotericin B 0.1 mmol derivative of Amphotericin B (A47) is suspended in 2 ml of deionized water in round-bottomed flask equipped with a magnetic stirrer. Next, to the reaction mixture 0.3 mmol of L-aspartic acid dissolved in 2 ml of water is added. The solution is filtered and to clear filtrate excess of acetone is added to precipitate. The resulting pale yellow precipitate is filtered under reduced pressure on a Millipore funnel. The crude product is twice washed with diethyl ether (2×50 ml) and then dried in a vacuum desiccator. In the manner described above exemplary is obtained 89 mg of 3-dimethylaminopropylamide N-D-β-(pirydyn-3-yl)alanylamphotericin B L-aspartate (A51)

UV-vis: $\lambda$max (MeOH) 406; 382; 363 nm; (MeOH, $\lambda$=406 nm)=1060 (theoretically for $C_{64}H_{100}N_6O_{21}$ is 1148) Below are shown the result of in vitro antifungal activity and hemotoxicity of Amphotericin B derivatives.

For the determination of antifungal activity in vitro we used method of serial dilution in buffered medium RPMI 1640, pH 7.0, in a 96-wells microplates, according to the standard procedure (National Committee for Clinical Laboratory Standards. Reference method for broth dilution antifungal susceptibility testing of yeast, approved standard, 2nd ed. M27-A2 vol. 22 Wayne, Pa., 2002). The optical density of cells suspension was measured using a microplates reader (Victor[3], Perkin-Elmer) at the wavelength $\lambda$=531 nm ($A_{531}$). On the basis of obtained results the diagrams of relation between $A_{531}$ values and concentration of examined compound were made. From these graphs, the $IC_{50}$ values were read, which were the interpolated concentrations of a tested compound, at which the $A_{531}$ value was exactly 50% of the $A_{531}$ value for the control sample. Moreover, MIC values, that are the lowest concentration of tested compound at which the $A_{531}$ value were at most 20% of the $A_{531}$ value measured for the control sample.

The hemotoxicity determination was carried out by the serial dilutions method, according to the procedure described earlier (Slisz, M., et al., E., *J Antibiot* 57: 669-678 (2004). Human erythrocytes were suspended in the solution of saline to obtain a cell density of suspension $2 \times 10^7$/ml. Suitable amounts of diluted solutions of compounds were added to the cell suspension in tubes and were incubated at 37° C. for 30 minutes and then centrifuged (1700×g, 10 min, 4° C.). The concentration of hemoglobin in supernatant after centrifugation of erythrocytes suspension were determined by measuring the absorbance at wavelength $\lambda$=540 nm ($A_{540}$). The maximum level of hemolysis was obtained after incubation of cells suspension in the presence of 0.1% Tritone X-100 (control sample). On the basis of obtained results the diagrams on relation between the $A_{540}$ value and concentration of examined compound were made. From these graphs, the $EH_{50}$ values were read which are the interpolated concentrations of compound, for which the $A_{540}$ value is exactly 50% of the $A_{540}$ value measured for the control sample. Maximum concentrations of tested derivatives could not exceed 100 μg/ml, to maintain full solubility in experimental conditions. At this maximum concentration of compounds which exhibited especially low hemotoxicity, it was not possible to determine the $EH_{50}$ value and in such cases was hemotoxicity specified as $EH_{50}$>100 μg/ml.

Obtained results are presented below in tables 2A and 2B. Table 2A presents the antifungal and hemolytic activity of a large series of Amphotericin B derivatives, additionally introducing factor describing the improvement of Amphotericin B derivatives selectivity in regard to the native antibiotic. WS factor determines the selectivity data of the derivatives, and WE factor shows the above selectivity data in regard to the same of the native Amphotericin B. Table 2B presents data concerning the broader antifungal spectrum of examined compounds.

TABLE 2A

| | | Antifungal activity [μg ml$^{-1}$] | | | | | | | | |
|---|---|---|---|---|---|---|---|---|---|---|
| | | *Saccharomyces cerevisiae* ATCC 9763 | | *Candida albicans* ATCC 10231 | *Candida tropicalis* KKP 334 | *Candida glabrata* DSM 11226 | *Candida krusei* DSM 6128 | *Candida lusitaniae* DSM 70102 | Hemotoxi [μg ml$^{-1}$] | WS $EH_{50}$/ | WE $WS_{(z)}$/ |
| No. | Symbol | MIC | IC$_{50}$ | MIC | MIC | MIC | MIC | MIC | $EH_{50}$ | IC$_{50}$ | $WS_{(AmB)}$ |
| 1. | AmB | 0.25 | 0.116 | 0.125 | 0.25 | 1 | 0.5 | 0.125 | 2.06 | 17.76 | 1 |
| 2. | A1 | 2 | 0.98 | 4 | 4 | 8 | 8 | 2 | >100 | >102.04 | >5.74 |
| 3. | A2 | 4 | 2.22 | 4 | 4 | 8 | 8 | 2 | >100 | >45.04 | >2.54 |
| 4. | A3 | 4 | 2.85 | 4 | 4 | 8 | 8 | 4 | >100 | >35.09 | >1.97 |
| 5. | A4 | 4 | 3.11 | 4 | 4 | 8 | 8 | 4 | >100 | >32.15 | >1.81 |
| 6. | A5 | 4 | 1.94 | 4 | 4 | 4 | 4 | 2 | >100 | >51.55 | >2.90 |
| 7. | A6 | 2 | 0.64 | 2 | 2 | 4 | 8 | 1 | >100 | >156.25 | >8.80 |
| 8. | A7 | 2 | 0.70 | 4 | 2 | 4 | 4 | 1 | >100 | >142.86 | >8.04 |
| 9. | A8 | 4 | 1.36 | 4 | 4 | 8 | 8 | 4 | >100 | >73.53 | >4.14 |
| 10. | A19 | 1 | 0.53 | 1 | 1 | 2 | 2 | 1 | >100 | >188.68 | >10.62 |
| 11. | A20 | 4 | 1.63 | 4 | 4 | 4 | 4 | 4 | >100 | >61.35 | >3.45 |
| 12. | A21 | 4 | 1.58 | 4 | 4 | 4 | 4 | 2 | >100 | >63.29 | >3.56 |
| 13. | A22 | 1 | 0.71 | 1 | 1 | 4 | 2 | 1 | >100 | >140.84 | >7.93 |
| 14. | A23 | 4 | 2.54 | 4 | 4 | 8 | 8 | 4 | >100 | >39.37 | >2.22 |
| 15. | A24 | 2 | 1.13 | 2 | 2 | 4 | 4 | 2 | >100 | >88.49 | >4.98 |
| 16. | A25 | 2 | 0.85 | 2 | 2 | 4 | 4 | 2 | >100 | >117.65 | >6.62 |
| 17. | A26 | 4 | 2.55 | 4 | 4 | 8 | 8 | 4 | >100 | >39.21 | >2.21 |
| 18. | A27 | 2 | 0.75 | 2 | 2 | 4 | 4 | 2 | >100 | >133.33 | >7.51 |
| 19. | A28 | 1 | 0.50 | 1 | 1 | 4 | 2 | 1 | 81.73 | 163.46 | 9.20 |

TABLE 2A-continued

| | | Antifungal activity [μg ml⁻¹] | | | | | | | | |
|---|---|---|---|---|---|---|---|---|---|---|
| | | Saccharomyces cerevisiae ATCC 9763 | | Candida albicans ATCC 10231 | Candida tropicalis KKP 334 | Candida glabrata DSM 11226 | Candida krusei DSM 6128 | Candida lusitaniae DSM 70102 | Hemotoxi [μg ml⁻¹] | WS EH$_{50}$/ | WE WS$_{(z)}$/ |
| No. | Symbol | MIC | IC$_{50}$ | MIC | MIC | MIC | MIC | MIC | EH$_{50}$ | IC$_{50}$ | WS$_{(AmB)}$ |
| 20. | A29 | 4 | 2.56 | 4 | 4 | 8 | 8 | 4 | >100 | >39.06 | >2.20 |
| 21. | A30 | 2 | 0.90 | 2 | 2 | 2 | 2 | 2 | >100 | >111.11 | >6.26 |
| 22. | A31 | 4 | 2.52 | 4 | 4 | 8 | 8 | 4 | >100 | >39.68 | >2.23 |
| 23. | A32 | 4 | 3.01 | 8 | 8 | 8 | 8 | 4 | >100 | >33.22 | >1.87 |
| 24. | A33 | 2 | 1.39 | 2 | 4 | 4 | 4 | 2 | >100 | >71.94 | >4.05 |
| 25. | A34 | 2 | 1.22 | 4 | 4 | 4 | 4 | 2 | >100 | >81.97 | >4.61 |
| 26. | A35 | 4 | 1.40 | 4 | 4 | 4 | 4 | 2 | >100 | >71.42 | >4.02 |
| 27. | A36 | 1 | 0.53 | 2 | 2 | 4 | 4 | 2 | >100 | >188.68 | >10.62 |
| 28. | A37 | 2 | 1.28 | 2 | 2 | 4 | 4 | 1 | >100 | >78.12 | >4.40 |
| 29. | A38 | 4 | 1.92 | 2 | 4 | 4 | 4 | 2 | >100 | >52.08 | >2.93 |
| 30. | A40 | 2 | 1.35 | 2 | 4 | 4 | 4 | 2 | >200 | >148.15 | >8.34 |
| 31. | A41 | 4 | 1.46 | 2 | 4 | 4 | 4 | 2 | >100 | >68.49 | >3.86 |
| 32. | A42 | 4 | 2.75 | 4 | 4 | 8 | 8 | 4 | >100 | >36.36 | >2.05 |
| 33. | A43 | 4 | 1.43 | 4 | 4 | 4 | 4 | 2 | >100 | >69.93 | >3.94 |

WS— selectivity coefficient
WE—effectivity factor
WS$_{(z)}$—selectivity coefficient for derivative
WS$_{(AmB)}$—selectivity coefficient for native antibiotic

TABLE 2B

| | | Antifungal activity MIC [μg ml⁻¹] | | | | | | | | | |
|---|---|---|---|---|---|---|---|---|---|---|---|
| L.p. | Symbol | Candida albicans SC 5314 | Candida pseudo-tropicalis KKP 324 | Candida stellatoidea CBS 1905 | Candida parapsilosis DSM 5784 | Candida dubliniensis CBS 7987 | Candida quilliermondii DSM 11947 | Candida arborea KKP 319 | Candida lipolytica KKP 322 | Aspergillus niger LOCK E201 | Trichoderma viride LOCK E159 |
| 1. | AmB | 0.5 | 0.25 | 0.25 | 0.5 | 0.25 | 0.25 | 1 | 0.5 | 0.25 | 0.5 |
| 2. | A19 | 0.5 | 0.5 | 1 | 2 | 0.5 | 2 | 2 | 2 | 1 | 4 |
| 3. | A22 | 2 | 2 | 1 | 2 | 1 | 1 | 2 | 1 | 2 | 2 |
| 4. | A30 | 1 | 1 | 1 | 2 | 1 | 1 | 4 | 2 | 2 | 4 |
| 5. | A33 | 1 | 1 | 1 | 1 | 1 | 1 | 2 | 1 | 1 | 4 |
| 6. | A34 | 1 | 1 | 1 | 1 | 1 | 2 | 4 | 1 | 2 | 4 |
| 7. | A36 | 1 | 1 | 2 | 2 | 1 | 1 | 4 | 2 | 0.5 | 4 |
| 8. | A41 | 1 | 2 | 2 | 2 | 1 | 1 | 4 | 2 | 2 | 4 |
| 9. | A42 | 4 | 4 | 4 | 4 | 2 | 4 | 4 | 4 | 1 | 2 |
| 10. | A43 | 1 | 2 | 1 | 1 | 1 | 1 | 8 | 1 | 1 | 4 |

Antifungal in vitro activity of Amphotericin B derivatives against multidrug resistant (MDR) fungal strains was also examined. The results are presented in table 3.

TABLE 3

| | | Antifungal activity MIC [μg ml⁻¹] Candida albicans clinical strains | | | | | | | |
|---|---|---|---|---|---|---|---|---|---|
| L.p. | Symbol | B3 | B4 | Gu4 | Gu5 (CaCdr1p, CaCdr2p) | F2 | F5 (CaMdr1p) | STY31 | STY7 (CaCdr1p) | 5674 (CaCdr1p, CaCdr2p) |
| 1. | AmB | 0.125 | 0.25 | 0.125 | 0.5 | 0.5 | 0.5 | 1 | 1 | 1 |
| 2. | A19 | 1 | 2 | 1 | 1 | 2 | 2 | 1 | 1 | 1 |
| 3. | A22 | 0.25 | 4 | 0.25 | 2 | 4 | 8 | 2 | 2 | 1 |
| 4. | A30 | 0.5 | 2 | 1 | 2 | 2 | 4 | 1 | 1 | 0.5 |
| 5. | A33 | 0.5 | 1 | 1 | 1 | 4 | 8 | 0.5 | 1 | 2 |
| 6. | A34 | 1 | 2 | 1 | 2 | 4 | 8 | 2 | 2 | 4 |
| 7. | A36 | 0.5 | 4 | 1 | 4 | 4 | 4 | 0.25 | 0.5 | 0.5 |
| 8. | A41 | 1 | 1 | 1 | 1 | 2 | 4 | 1 | 1 | 1 |
| 9. | A42 | 2 | 8 | 2 | 4 | 1 | 2 | 4 | 4 | 4 |
| 10. | A43 | 0.5 | 1 | 1 | 2 | 4 | 4 | 1 | 0.5 | 1 |

| Strains | Description | Reference |
|---|---|---|
| | *Candida albicans* clinical isolates | |
| B3 | fluconazole sensitive, parent strain for B4 | 1 |
| B4 | fluconazole-resistant due to the overexpression of CaMDR1 | 1 |
| Gu4 | fluconazole sensitive, parent strain for Gu5 | 1 |
| Gu5 | fluconazole-resistant due to the overexpression of CDR1 and CDR2 | 1 |
| F2 | fluconazole sensitive, parent strain for F5 | 2 |
| F5 | fluconazole-resistant due to the overexpression of CaMDR1 and ERG11 | 2 |
| STY7 | *C. albicans* 5674 overexpressing CDR1 and CDR2 mutant derivative, deletion of CDR2 | 3 |
| STY31 | *C. albicans* 5674 overexpressing CDR1 and CDR2 mutant derivative, deletion of CDR1 and CDR2 | 3 |

References:
1. Franz, R., Ruhnke M, Morschhäuser J. 1999 Molecular aspects of fluconazole resistance development in *Candida albicans*. Mycoses, 42, 453-458.
2. Franz, R., Kelly S. L., Lamb D. C., Kelly D. E., Ruhnke M., Morschhäuser J. 1998. Multiple molecular mechanisms contribute to a stepwise development of fluconazole resistance in Clinical *Candida albicans* strains. Antimicrobial Agents and Chemotherapy 42: 3065-3072.
3. Tsao S., Rahkhoodaee F., Raymond M. 2009. Relative contributions of the *Candida albicans* ABC transporters Cdr1p and Cdr2p to clinical azole resistance. Antimicrobial Agents and Chemotherapy 53: 1344-1352.

Cytotoxic activity of Amphotericin B derivatives against mammalian cells was determined in tissue culture.
For examinations were used selected cell lines: CCRF-CEM—human acute lymphoblastic leukemia; HepG2—human malignant hepatoma; LLC-PK1—epithelial cell of pig kidney; All lines were from ATCC collection.
The study was conducted using described below methods of culturing and determination of cytotoxic activity.
CCRF-CEM cells were cultured in medium RPMI 1640+ 10% fetal bovine serum (FBS), LLC-PK1 cells in medium Medium 199+3% FBS, HepG2 cells in medium MEM+ 10% FBS. All media contained 100 µg/ml of penicillin G and streptomycin. 24-wells microplates containing appropriate medium were inoculated with the cells in amount of $1.2 \times 10^4$ cells/well and allowed to stand overnight. Next, tested compounds as solution in dimethylsulfoxide (DMSO) were added in volume of 10 µl (serial 2× dilutions). To control well 10 µl of DMSO was added. Microplates with cell suspensions were incubated for 120 h at temperature 37° C. at atmosphere of 95%/5% $CO_2$. After incubation, to all wells 200 µl of solution of 3-(4,5-dimethyltiazole-2-yl)-2,5-diphenylotetrazole bromide (MTT) in PBS (4 mg/ml) was added and plates were further incubated for 4 h at 37° C. Next, to dissolve crystals of formazane 1 ml of DMSO was added and absorption of solutions was measured at the wavelength $\lambda=540$ nm ($A_{540}$), using a microplates reader (Victor³, Perkin-Wallac). On the basis of received results the diagrams on the relation between the $A_{540}$ value and concentration of examined compound were prepared. From these graphs $IC_{50}$ values were read, that is concentration of tested compound in the presence at which $A_{540}$ value is half of $A_{540}$ value measured in the control sample.
The obtained results are presented in Table 4.

TABLE 4

| | $IC_{50}$ [µg/ml] | | |
|---|---|---|---|
| Compound | HepG2 | LLC-PK1 | CCRF-CEM |
| Amfotericin B (Fungizon) | 5.40 ± 1.05 | 19.7 ± 8.05 | 4.30 ± 0.86 |
| A-6 | >100 | >100 | >100 |
| A-16 | 73.3 ± 1.20 | >100 | 50.1 ± 1.3 |
| A-19 | >100 | >100 | >100 |

TABLE 4-continued

| | $IC_{50}$ [µg/ml] | | |
|---|---|---|---|
| Compound | HepG2 | LLC-PK1 | CCRF-CEM |
| A-22 | >100 | >100 | >100 |
| A-24 | >100 | >100 | 80.9 ± 2.3 |
| A-25 | >100 | >100 | >100 |
| A-27 | >100 | >100 | >100 |
| A-28 | >100 | >100 | >100 |
| A-30 | >100 | >100 | >100 |
| A-33 | >100 | >100 | >100 |
| A-34 | >100 | >100 | >100 |
| A-35 | >100 | 70.7 ± 2.3 | >100 |
| A-36 | >100 | >100 | >100 |
| A-41 | >100 | >100 | >100 |
| A-42 | >100 | >100 | >100 |
| A-43 | >100 | >100 | >100 |

The invention claimed is:
1. A compound of Formula 1a

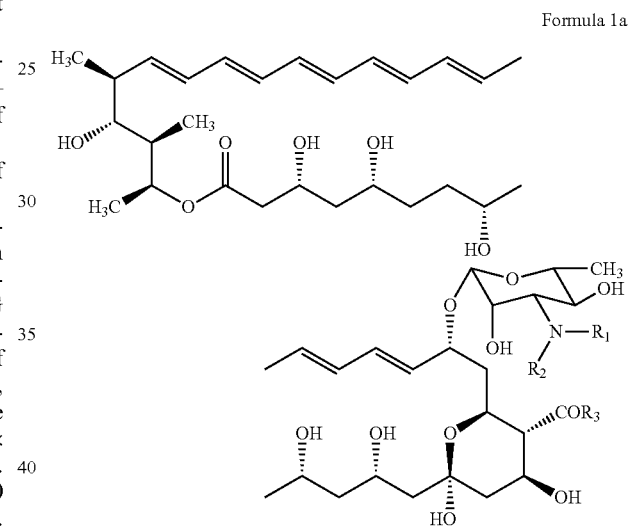

Formula 1a or a salt, hydrate or complex thereof;
wherein $R_1$ is:
a) a thioureidyl residue of structure

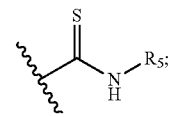

wherein
$R_5$ is —W—Z;
W is an optionally substituted alkyl linker or a bond;
Z is an optionally substituted aryl, heteroaryl, nitrogen-containing heterocycloaliphatic, $NR^*_2$, $NH_2$ or $NHR^*$; and
$R^*$ is an optionally substituted aliphatic moiety, an optionally substituted carbocyclic moiety, or an optionally substituted heterocyclic moiety; or alternatively two $R^*$, together with the nitrogen atom to which they are bound, form an optionally substituted heterocycle, wherein Z is optionally substituted with one or more of alkyl or halo; or b) benzyl substituted with one or more substituents selected from optionally substituted carbocycle, optionally substituted heterocycle, branched $C_{3-6}$alkyl, or dialkylamino;

$R_2$ is a hydrogen atom, an unsubstituted non-branched alkyl, a substituted alkyl, or one of the substituents as defined in $R_1$;

$R_3$ is a hydroxyl group, alkoxyl group, alkylamino, or —$NR_{14}$—($C_1$-$C_6$alkyl)-$NR_{15}R_{16}$, wherein $R_{14}$ is a hydrogen atom or methyl, and $R_{15}$ and $R_{16}$ are independently chosen from hydrogen or optionally substituted aliphatic.

2. A compound according to claim 1, wherein $R_2$ is a hydrogen atom, a non-branched alkyl, or alkyl substituted with alkylamino or an optionally substituted carbocyclic or N-containing heterocyclic moiety.

3. A compound according to claim 1, wherein $R_3$ is hydroxyl, methoxy, or —$NR_{14}$—($C_1$-$C_6$alkyl)-$NR_{15}R_{16}$, wherein $R_{14}$ is a hydrogen atom or methyl, $R_{15}$ and $R_{16}$ are independently chosen from hydrogen or optionally substituted aliphatic.

4. A compound according to claim 1, selected from: N-[3-(2-piperidin-1-ylethyl)-thioureidyl]amphotericin B, N-[(3-phenyl)thioureidyl]amphotericin B, N-[3-(2-morpholin-1-ylethylo)thioureidyl]amphotericin B, N-{3-[2-(N,N-diethylamino)ethyl]thioureidyl}amphotericin B, N-[3-(pyridin-3-yl)thioureidyl]amphotericin B, N-[3-(2-pirrolidin-1-ylethyl)thioureidyl]amphotericin B, N-{3-[2-(N,N-dimethylamino)ethyl]thioureidyl}-amphotericin B, N-[3-(pyridin-4-ylmethyl)thioureidyl]amphotericin B, N-(4-N,N-diethylaminobenzyl)amphotericin B, N-[(4-biphenyl)-methyl]amphotericin B, N-(4-tert-butylbenzyl)amphotericin B, N-[3-(2-piperidin-1-yl)ethyl]thioureidyl}amphotericin B methyl ester, N-(4-N,N-diethylaminobenzyl)amphotericin B methyl ester, N-{[3-(2-piperidin-1-yl)ethyl]thioureidyl]amphotericin B 3-(N,N-dimethylamino)propylamide, N-(4-N,N-diethylaminobenzyl)amphotericin B 3-(N,N-dimetyloamino)propylamide or a salt, hydrate or complex thereof.

5. A compound, according to claim 1, in the form of a salt with an inorganic or organic base or an inorganic or organic acid.

6. A compound, according to claim 1, in the form of a complex with an inorganic or organic complexing compound.

7. A pharmaceutical composition comprising a compound of claim 1.

8. A method for treating fungal infection in a patient comprising administering to the patient a therapeutically effective amount of a compound according to claim 1, wherein the patient is a human or animal.

9. A method of treating fungal infection in a plant, comprising administering a compound according to claim 1 to a plant.

10. A method of treating a building comprising administering a compound according to claim 1 to a building.

11. A method of treatment as claimed in claim 8, wherein the fungal infection is caused by pathogenic fungi from the group of yeasts and filamentous fungi or a strain of the genus *Candida*.

12. A compound selected from the group consisting of:
N-[N-(2,4,6-trimethylphenyl)succinimidyl]amphotericin B,
N-(N-benzylsuccinimidyl)amphotericin B,
N-[N-(4-bromophenyl)succinimidyl]amphotericin B,
N-[N-(2-tert-butylphenyl)succinimidyl]amphotericin B,
N-[N-(4-nitrophenyl)succinimidyl]amphotericin B,
N-[N-(2-piperidn-1-ylethyl)succinimidyl]amphotericin B,
N-{N-[3-(N,N-dimethylamino)-2,2-dimethylpropyl]succinimidyl}amphotericin B,
N-[N-(2-hydroxyethyl)succinimidyl]amphotericin B,
N,N-dimethylamphotericin B,
N,N-diethylamphotericin B,
N,N-di-n-propylamphotericin B,
N,N-di[3-(N-piperidin-1-yl)propyl]amphotericin B,
N,N-di[3-(4-ethylpiperazin-1-yl)propyl]amphotericin B,
N-ethyl-N-fructosylamphotericin B,
N-fructosyl-N-n-propylamphotericin B,
N-fructosyl-N-(N,N-dimethyl-3-aminopropyl)amphotericin B,
N-fructosyl-N[3-(piperidin-1-yl)aminopropyl]amphotericin B,
N-L-phenylalanyloamphotericin B,
N-L-p-iodophenylalanylamphotericin B,
N-D-β-naphtylalanylamphotericin B,
N-L-p-nitrophenylalanylamphotericin B,
N-methyl-L-($O^\gamma$-tert-butyl)glutamylamphotericin B,
N-D-($O^\beta$-tert-butyl)asparagylamphotericin B,
N-D-β-(pyridin-3-yl)alanylamphotericin B,
N-L-(S-tert-butyl)cystylamphotericin B,
N-o-fluorophenylalanylamphotericin B,
N-D-($O^\gamma$-tert-butyl)glutamylamphotericin B,
N-D-(O-tert-butyl)serylamphotericin B,
N-D-phenylglycylamphotericin B,
N-(L-N,N-diethylphenylalanyl)amphotericin B,
N-D-β-(pyridin-3-yl)alanylamphotericin B methyl ester, and
N-D-β-(pyridin-3-yl)alanylamphotericin B 3-(N,N-dimethylamino)propylamide,
or a salt, hydrate or complex thereof.

* * * * *